(12) United States Patent
Sarkissian

(10) Patent No.: US 8,123,029 B2
(45) Date of Patent: Feb. 28, 2012

(54) BABY TOOTH ALBUM

(76) Inventor: Robert Sarkissian, Northridge, CA (US)

(*) Notice: Subject to any disclaimer, the term of this patent is extended or adjusted under 35 U.S.C. 154(b) by 541 days.

(21) Appl. No.: 11/598,867

(22) Filed: Nov. 14, 2006

(65) Prior Publication Data

US 2008/0110776 A1    May 15, 2008

(51) Int. Cl.
B65D 71/00    (2006.01)

(52) U.S. Cl. .................. 206/83; 206/63.5; 206/459.5

(58) Field of Classification Search .................. 206/83, 206/63.5, 756, 459.1, 461, 467, 472–473, 206/538, 505, 533–534, 539, 459.5
See application file for complete search history.

(56) References Cited

U.S. PATENT DOCUMENTS

| | | | | |
|---|---|---|---|---|
| 3,743,085 A | * | 7/1973 | Richert | 206/534 |
| 4,124,143 A | * | 11/1978 | Thomas | 221/82 |
| D284,227 S | | 6/1986 | Dagowitz | |
| 4,694,956 A | | 9/1987 | Sims | |
| 4,777,745 A | | 10/1988 | Rose | |
| 4,923,058 A | | 5/1990 | Dennison | |
| 5,050,729 A | | 9/1991 | Karbowniczak | |
| 5,055,079 A | | 10/1991 | Hobson et al. | |
| 5,303,819 A | | 4/1994 | Goldbert | |
| 5,394,989 A | | 3/1995 | Delson | |
| 5,621,990 A | | 4/1997 | Blanchard | |
| 5,938,242 A | | 8/1999 | Ryan | |
| 6,039,495 A | | 3/2000 | Zimmerman et al. | |
| 6,302,777 B1 | | 10/2001 | Zoldan | |
| 6,932,213 B1 | * | 8/2005 | Distad | 206/83 |
| 7,090,073 B2 | | 8/2006 | Barnes | |
| 2004/0011698 A1 | * | 1/2004 | Gaffney et al. | 206/704 |
| 2005/0109659 A1 | * | 5/2005 | Hickey et al. | 206/538 |
| 2005/0258066 A1 | * | 11/2005 | Conley | 206/538 |

FOREIGN PATENT DOCUMENTS

GB    2187715    9/1987

* cited by examiner

*Primary Examiner* — J. Gregory Pickett
*Assistant Examiner* — Robert Poon
(74) *Attorney, Agent, or Firm* — Thomas I. Rozsa

(57) ABSTRACT

A simple, lightweight, inexpensive and adaptable display container specifically designed to display all of a baby's teeth from nearly any angle. The invention displays the teeth with respect to each tooth's position in the mouth and has a transparent cover that completely encloses all the teeth and does not need to leave one or two teeth partially uncovered. The invention permits the cover to lock in place, either over the cell in which the tooth is placed or over a non-cell surface so that all the cells for the teeth are completely covered and protected. The invention also permits the displayed tooth to be situated close to the underside of the cover to maximize the display of the tooth and permits the baby tooth display to be incorporated into other display devices, such as frames, three-ring binders, scrapbooks, photo albums, and baby albums.

24 Claims, 9 Drawing Sheets

BABY TOOTH ALBUM

BACKGROUND OF THE INVENTION

1. Field of the Invention

This invention relates generally to the field of display cases and albums for retaining and displaying a variety of items and for cases and albums to retain memorabilia.

2. Description of the Prior Art

In general, receptacles for teeth, both mouth-morphic and plain, are known in the prior art. Parents are searching for a means to save those precious and sentimental mementos of their child. Often parents resort to using pill bottles or small tins to save the teeth, which makes it difficult to display the teeth and also has the effect of jumbling the teeth, so that parents don't know when a tooth came out, or where the tooth was in the child's mouth.

Additionally, the rise in creativity of parents and grandparents involves them in trying to frame the baby teeth or place the teeth in a scrapbook or create some type of display for these mementos.

The following fourteen (14) utility patents and one (1) design patent are relevant to the field of the present invention.

1. U.S. Pat. No. 4,694,956 issued to Edward H. Sims on Sep. 22, 1987 for "Display Receptacle For Deciduous Teeth" (hereafter the "Sims Patent");
2. U.S. Pat. No. 4,777,745 issued to Carolyn A. Rose on Oct. 18, 1988 for "Tooth Storage And Display Apparatus" (hereafter the "Rose Patent");
3. U.S. Pat. No. 4,923,058 issued to Mary R. Dennison on May 8, 1990 for "Container For Storing And Displaying Baby Teeth" (hereafter the "Dennison Patent");
4. U.S. Pat. No. 5,050,729 issued to Edith M. Karbowniczak on Sep. 24, 1991 for "Tooth Storage Container" (hereafter the "Karbowniczak Patent");
5. U.S. Pat. No. 5,055,079 issued to Philip H. Hobson et al. on Oct. 8, 1991 for "Coin Bank With Separations And Turnable Top" (hereafter the "Hobson Patent");
6. U.S. Pat. No. 5,303,819 issued to Eileen S. Goldberg on Apr. 19, 1994 for "Display Holder For Teeth" (hereafter the "Goldberg Patent");
7. U.S. Pat. No. 5,394,989 issued to Donn M. Delson on Mar. 7, 1995 for "Castle With Storage Compartment" (hereafter the "Delson Patent");
8. U.S. Pat. No. 5,621,990 issued to Anastasia Blanchard on Apr. 8-22, 1997 for "Keepsake Holder For Baby Teeth" (hereafter the "Blanchard Patent");
9. U.S. Pat. No. 5,938,242 issued to Jennifer L. Ryan on Aug. 17, 1999 for "Multiple Media Storage Device For Book Leaf Structure" (hereafter the "Ryan Patent");
10. U.S. Pat. No. 6,039,495 issued to Julie G. Zimmerman et al. and assigned to Kallman Corporation on Mar. 21, 2000 for "Storage Page For Three-Dimensional Items" (hereafter the "Zimmerman Patent");
11. U.S. Pat. No. 6,302,777 issued to Romeo Zoldan and assigned to Unitylab Inc. on Oct. 16, 2001 for "Coin Holder" (hereafter the "Zoldan Patent");
12. U.S. Pat. No. 6,932,213 issued to Elaine Sandra Fram Distad on Aug. 23, 2005 for "Baby Teeth Collection Box With Pillow Toothbox" (hereafter the "Distad Patent");
13. U.S. Pat. No. 7,090,073 issued to Richard Barnes and assigned to Dick Barnes Group on Aug. 15, 2006 for "Dental Tray Assembly" (hereafter the "Barnes Patent");
14. UK Patent Application No. GB 2,187,715 issued to Daniel V. Breslin on Sep. 16, 1987 for "Tooth Storing Means" (hereafter the "Breslin Patent"); and
15. U.S. Pat. No. D284, 227 issued to Steven Dagowitz and Gail Dagowitz on Jun. 10, 1986 for "Combined Tooth Saver and Coin Bank" (hereafter the "Dagowitz Patent").

The Sims Patent discloses a display receptacle for deciduous teeth. Essentially it involves a housing that is in the form of the shape of a pair of false teeth with members in which each individual tooth can be inserted and retained. Each member is releasably closed around the circumference of the mouth.

Referring to the Sims Patent, the preferred embodiment of the display receptacle shown in FIG. 1 appears to show that each receptacle is removable from the display and can therefore be lost. Additionally, though it displays each tooth separately, the teeth cannot all be simultaneously viewed without manipulation of the receptacle. Furthermore, the display receptacle is too large and bulky to be added to an album and is too awkward to be framed. Moreover, the receptacles for each tooth are of the same height with the upper teeth stored so that they rest on the bottom of the receptacle and the bottom teeth resting on the top of the receptacle, thus making viewing and accessing the teeth difficult. In addition, the display receptacles with separate tooth receptacles and hinged mouth shaped holders are more complex and expensive to manufacture than a single molded container. In addition, there is no accommodation for recording or memorializing the event of the lost tooth.

The Rose Patent discloses the concept of having a picture frame with a picture that could, for example, be the tooth fairy which can be lifted out as shown in FIG. 2 to expose a retaining member which contains retainers for retaining each tooth as well as notes to write about the tooth and when the tooth fell out and anything else as well as an opportunity to retain the child's picture in the center of the tooth storage.

Referring to the Rose Patent, the preferred embodiment of the display shown in FIGS. 1 and 2, appears to show that the primary display is that of the "tooth fairy" or some other picture with the baby teeth stored and hidden behind this picture. Although it stores the teeth in a manner consistent with the teeth's placement in the mouth, adding a tooth to be stored requires the display to be taken apart and then a reconstruction of the various layers to return it to its former condition after the tooth has been added. Furthermore, this is more complex and expensive to manufacture than a single molded container with a single molded cover.

The Dennison Patent discloses a container for storing and displaying baby teeth. The container includes a hollow body and a hinged cover. An insert in the body is formed with 20 upwardly opened pockets for receiving a set of 20 baby teeth. The pockets are sized in accordance with the size of the different types of teeth. In addition, the pockets are arranged such that when the teeth are stored their replacement assimilates the placement of the teeth in the upper and lower jaws.

Referring to the Dennison Patent, the preferred embodiment of the container shown in FIGS. 2 and 3, appears to hold the teeth not in the manner in which the teeth reside in the mouth, but rather in a circular pattern with the four molars in the center of this ring. Additionally, when the container is opened to view the teeth, all the teeth are exposed and in danger of becoming lost. Furthermore, there is no accommodation for recording or memorializing the event of the lost tooth and this apparatus is more complex and expensive to manufacture than a single molded container with a single molded cover.

The Karbowiniczak Patent discloses a pocket for retaining an individual tooth with means to secure the tooth within the pocket and also a peel away means so that the tooth can be viewed within the pocket.

Referring to the Karbowiniczak Patent, the preferred embodiment as shown in FIGS. 1, 5 and 6, appears to hold only one tooth and does not have a place on which to memorialize the occasion of the loss of the tooth. Additionally, the display of all twenty deciduous teeth requires twenty separate pockets and is too bulky and too large to display on one page in an album.

The Hobson Patent discloses a coin bank. It contains the concept of having individual slots contained within a receptacle and a rotatable means so that the receptacle can be rotated to a given location wherein a coin can be dropped into an individual slot. This patent discloses the concept of a rotatable top with an opening for inserting a member into a multiplicity of divided sections within the container.

Referring to the Hobson Patent, the preferred embodiment of the coin bank as shown in FIG. 1 appears to show a freely rotating cover 20 having a slot 108 through which the coin enters the bank, with no means of locking or holding the cover or the slot in any particular position. Furthermore, this coin bank is made of numerous parts and is more complex and expensive to manufacture than a single molded container with a single molded cover. It also does not have a low profile and is not lightweight enough to be put in a scrapbook or photo album.

In the Goldberg Patent, "a tooth holder is provided with U-shaped storage members that have multiple transparent compartments each accommodating a particular tooth. Each storage member includes a base in which a set of the compartments are formed and a detachable cover therefor. The cover snaps on top of a respective base to hold the teeth in the compartments in place. The storage members are secured to a casing having a hinge such that the storage members can be pivoted and secured one on top of the other for storage. The casing includes a shelf that extends beyond each base so that a label indicating the date of tooth loss can be placed on the shelf adjacent the compartment in which the tooth is placed." This patent discloses the concept of having a transparent compartment to retain the teeth and means for having notations on when the tooth fell out on a circumference around the teeth. The device simulates the mouth and basically has a hingeable cover that folds over.

Referring to the Goldberg Patent, the preferred embodiment as shown in FIGS. 4, 5, shows a cover member 14, 16 with a depression 15, 17 to cover the entirety of the lower compartments and the entirety of the upper compartments. Adding a tooth to either the lower compartments or the upper compartments requires the removal of the cover member, thus uncovering all the compartments in that section. Furthermore, the preferred embodiment as shown in FIG. 1 does not allow for the viewing of all the teeth simultaneously without manipulation of the device and if made of a transparent plastic would allow viewing of only one compartment. The device also cannot be placed in a photo album or scrapbook.

The Delson Patent is a castle structure which contains a central storage compartment. It provides a means to store a container that is used in conjunction with a tooth fairy bed time story so that the tooth can be placed in the container when alternatively a dollar bill or some other compensation to the child is provided with the tooth.

Referring to the Delson Patent, the preferred embodiment of the castle as shown in FIG. 1 appears to show a single receptacle for storing all the teeth, rather than a receptacle for each individual tooth, so that all the teeth stored may rattle around and become damaged. Additionally, there is no means to memorialize each tooth nor is there a means to identify each tooth. Moreover, the main display is that of a castle and is not meant to be part of an album or scrapbook. Furthermore, this castle is made of numerous parts and is more complex and expensive to manufacture than a single molded container with a single molded cover.

The Blanchard Patent is a keepsake holder for baby teeth and once again employs the concept of having a means to save the baby's tooth as well as a means to record information about when each tooth came out. Specifically, it is a keepsake holder for baby teeth which provides parents, guardians and others with a convenient way in which to save and display a child's baby teeth. The holder comprises a generally folded card having a top leaf and a bottom leaf. Attached to the inside of the top leaf are preferably graphical representations and dental terminology indicia corresponding to a child's twenty baby teeth. Attached to the bottom leaf is a plurality of date entry lines for entering the dates on the sheet that a child's baby tooth fell out. Also attached to the bottom leaf is a multi-pocketed double ply transparent sheet for separately retaining the child's baby teeth. Cross-referencing indicia are disposed adjacent each graphical representation, dental terminology indicia, data entry line and pocket to cross-reference each baby tooth to its graphical representation, its dental terminology and the date it fell out.

Referring to the Blanchard Patent, the preferred embodiment of the keepsake holder as shown in FIG. 2, appears to show the "identifying means 50 also comprises dental terminology indicia 54 of a child's baby teeth" which is adjacent to the tooth retainer, not incorporated within it. This is just a folded card with pockets for each tooth, and as such does not offer durability as molded plastic does. Should the top leaf become removed from the keepsake holder, the tooth indicia information is lost. Additionally, the teeth are stored in the order they come out and are numbered such that the first tooth to come out is number 1, the second tooth is number 2, and so on, rather than stored in the order they appear in the mouth. Furthermore, this keepsake holder is made of numerous parts and is more complex and expensive to manufacture than a single molded container with a single molded cover.

The Ryan Patent is a multiple media storage device for book leaf structures. In this invention a multiple media storage device is for attachment to a conventional book leaf. The device includes a two dimensional storage compartment and/or three dimensional storage compartment which has an optional data entry area associated with the storage compartments. The data entry area is a writing area provided for entry of printed information on the device. The device is attached to a conventional book leaf via a substrate that holds the integral storage compartments and data entry areas being adhered to the surface of the book leaf. An alternative embodiment integrates the device into a book leaf structure. The book leaf structure may have multiple devices on a single page, each of which may hold entry areas for printed information related to objects in the storage compartments. The storage compartments may be transparent to allow viewing the contents without opening the storage compartment. Optional leaf structures provide storage compartments which are exposed on both sides of the leaf to allow viewing the contents of the storage compartment from both sides. The storage compartments may be sealed such that the contents of the storage compartments are protected from environmental damage.

In referring to the Ryan Patent, preferred embodiment of the storage device, as shown in FIG. 2, appears to show that the storage device protrudes from both the front and back side of the page, rather than lying flat on the page. The cover for the storage device is a single piece that encompasses the entirety of the storage device and is designed so that access to one pocket requires removal of the device from the three-ring binder and allows all pockets to be opened simultaneously.

The Zimmerman Patent discloses the concept of a storage page for a three ring binder which has a plurality of three dimensional cavities for storing and displaying three dimensional objects. However, access to a cavity requires removal from the display device, such as a three-ring binder, and removal of the cover which will open all the other cavities on the storage page, rather than access to only one cavity.

The Zoldan Patent discloses a coin holder which has a rotatable cover with an opening that enables a coin to be dropped into a given section within the coin holder. However, the coin holder is not a display device and merely vertically stacks coins, one upon the other. Additionally, the coin holder is not adaptable to display itself in a frame or scrapbook. Furthermore, this keepsake holder is made of numerous parts and is more complex and expensive to manufacture than a single molded container with a single molded cover.

U.S. Pat. No. 6,932,213 issued to Distad discloses a "Baby Teeth Collector Box With Pillow Toothbox." It discloses a circular box with dividing portions in the box in order to enable individual teeth to be segregated. There is also a card on the bottom of the box which has a photograph and pictures to show which specific tooth is placed in that slot and an area in which notes can be made about the tooth. In addition to that, there is a shield card 86 which is placed within the box and when the box is inverted the shield card permits a particular tooth to be examined relative to the location where it is indicated as to what tooth it was. In addition to that, the box has a cover which can be removable.

In referring to the Distad Patent, a preferred embodiment of the collector box appears to show a cover that is solid and opaque and must be lifted off the box, thereby exposing all the compartments when attempting to add or extract a tooth. The cover does not rotate around the compartments nor is there an aperture in the cover to access one tooth, while protecting the others. Additionally, while the shape of each compartment may vary, the depth of each compartment does not. In addition, the notes and indications for each tooth are retained within each compartment of the collector box, rather than affixed to the device, so it is easier to associate the recorded information without having to lift off the cover and remove the tooth. The device also cannot be accommodated I a photo album or scrapbook.

The Barnes Patent is a dental tray which basically retains dental prosthetics and has a cover which protects the prosthetics. The cover can be retracted to expose one or more of the prosthetics. However, the cover does not rotate and it allows access to all compartments simultaneously. Additionally, the dental tray has an opaque two-layer cover that prevents viewing of items unless the cover is open. In addition, there is no means to record notations regarding that which is being stored, nor any indications of how the prosthetics should be stored. Furthermore, this keepsake holder is made of numerous parts and is more complex and expensive to manufacture than a single molded container with a single molded cover.

The United Kingdom Patent application was published in 1987 and is a tooth storing means. It has the picture of a mouth where teeth can be stored and a means for showing when the teeth were placed in the structure.

Referring to the United Kingdom Patent, the preferred embodiment of the tooth storing means shown in FIG. 1 appears to show that access to add to or extract from each tooth element is by a sliding lid that opens all ten tooth elements at a time. Additionally, although it displays each tooth separately, the teeth cannot all be seen simultaneously without manipulation of the receptacle. In addition, viewing is further impeded by the gum and lips added to the frontal viewing area, as shown in FIGS. 1 and 5. Furthermore, the tooth storing means is too large and bulky to be added to an album and is too awkward to be framed. Moreover, the tooth elements for each tooth are of the same height with the upper teeth stored so that they rest on the bottom of the receptacle and the bottom teeth resting on the top of the receptacle, thus making viewing and accessing the teeth difficult. In addition, the tooth storing means with separate tooth elements and hinged mouth shaped holders are more complex and expensive to manufacture than a single molded container.

The Dagowitz Patent, as sold in its current form, is a resin bank in the shape of a giant tooth resting atop a hard resin pillow. On the pillow at the base of the tooth are twenty (20) recessed receptacles all of the same size and depth, numbered 1 through 20, to indicate the order in which the tooth that fell out and topped by a revolving see-through plastic with a number. On the underside of the pillow is a sticker on which notations may be made regarding the tooth with reference to the tooth limited to the order number.

Referring to the Dagowitz Patent, the present embodiment does not have a closing space over which to place the aperture, with the result that the present embodiment has its aperture resting over the opening of at least one and sometimes two of the receptacles. In addition, the size of the tooth in the center of the pillow is such that the teeth cannot be viewed simultaneously, except from a one view only: a direct overhead view where the tooth in the center still impedes viewing. Moreover, all receptacles have identical size and depth. In addition, the aperture does not have a flange to hold its position over a receptacle. Additionally, there is no means to differentiate between the upper and lower teeth. Moreover, while there is a recording device on the bottom, the recording device does not correlate to the receptacle above it nor is there a means to determine which receptacle is above the recording area. To determine which receptacle and tooth is being referenced requires that the teeth to be removed to see the number on the bottom of the receptacle. Furthermore, the tooth saver is not adaptable to be framed or placed in an album or scrapbook. In addition, the tooth saver is more complex and expensive to manufacture than a single molded container.

Storage devices with multiple compartments such as those found in dental supplies exist in the prior art. These are generally for the purpose of storing braces, brackets and prosthetics. However, the compartments for these are not sized for baby teeth. Additionally, these containers do not generally include a means for viewing while simultaneously protecting that which is stored. Further, these containers are not adaptable for placement in scrapbooks, albums or frames. Moreover, these storage devices are generally comprised of multiple parts and are more complex and expensive to manufacture than a single molded container.

Storage devices with multiple compartments to store teeth in the manner in which teeth are placed in the mouth exist in the prior art. However, these compartments do not display the teeth equally, as the teeth in the upper portion are easily seen because they rest on the bottom of the compartment in which they reside, whereas the teeth in the lower portion of the display, rest on the underside of the top of their compartments, due to gravity, and are not as visible because these teeth are resting below the "gum line." Visibility of the teeth is further impeded when additions to the front are added, such as "gums" and "lips." Additionally, these devices generally do not allow all the teeth to be seen at the same time. For example, when viewing the right molars, the teeth on the left side cannot be seen. In addition, these devices generally lack the combination of a means to identify the tooth, a means to memorialize the event, and a cover that allows access to only one tooth at a time. Further, these containers are not adaptable for placement in scrapbooks, albums or frames. Moreover, these containers are comprised of a multiplicity of parts and are more complex and expensive to manufacture than a single molded container.

Storage devices with multiple compartments such as those found in craft stores exist in the prior art. These compartments are generally designed for the purpose of storing sewing or craft supplies. However, these compartments are too large for storing a single tooth. Additionally, access to one compartment generally entails removal of the lid which covers all the compartments, thus exposing all the compartments and making their contents vulnerable to damage and loss.

Tooth storage devices with multiple compartments such as those found in toy stores exist in the prior art. These compartments are generally designed with a primary purpose to enhance the toy aspect of the storage device, with the storage of the teeth a secondary function, and with the viewing of the teeth, last, if at all. Additionally, such devices are too large and bulky to be added to an album or cannot be framed. Further, these compartments are not designed for individual teeth; either there is one giant compartment for one or more teeth or all the compartments are the same size and shape without differentiation for larger and smaller teeth. Moreover, the teeth storage devices do not include a transparent cover that has the ability to cover all compartments simultaneously, nor do such devices have the ability to view all the teeth at the same time from a multiplicity of angles, nor do these devices have a cover with an aperture that can lock in place. Moreover, these containers are comprised of a multiplicity of parts and are more complex and expensive to manufacture than a single molded container.

Rotating lids on storage devices with multiple compartments such as those found in toy and novelty stores exist in the prior art. These lids are generally designed for the purpose of adding a coin to the bank. However, these rotating lids are generally not designed to display that which is stored and are usually opaque, relying on the sides of the container to be transparent for viewing. In some cases, there is no provision for viewing the stored items. In addition, the rotating lid has no mechanism to keep it in a particular place, thus allowing the lid and its aperture to move freely over the compartments, thereby allowing anything to enter or exit the compartments. Moreover, the apertures generally do not have a closing position, wherein the aperture is not in position over a storage compartment. In addition, these rotating lids are not the means through which the stored items are viewed, nor do these lids lend themselves to adaptability into a frame or an album. Moreover, these containers are comprised of a multiplicity of parts and are more complex and expensive to manufacture than a single molded container.

There is a significant need for an improved baby tooth holder to retain a child's baby teeth for posterity.

OBJECTS AND ADVANTAGES

Accordingly, several objects and advantages of the present invention are listed below.

First, it is an object to provide a baby teeth display which contains smaller receptacles each holding a single tooth, having the ability to be viewed from a multiplicity of angles. The present invention provides all of these features.

Second, it is an object of the invention to provide a teeth display container with a cover that protects the teeth and allows access to only one receptacle, and thus only one tooth, at a time. The present invention provides all of these features.

Third, it is an object of the invention to provide a teeth display container with receptacles for each tooth, with each receptacle at differing depths in relation to the tooth placed within it. The present invention provides all of these features.

Fourth, it is an object of the invention to provide a teeth display container with a clear rotatable cover through which the teeth may be viewed and which provides means by which the aperture is not over any of the receptacles, either partially or fully. The present invention provides all of these features.

Fifth, it is an object of the invention to provide a teeth display container with a clear rotatable cover that has a means by which the cover is inhibited from freely rotating. The present invention provides all of these features.

Sixth, it is an object of the invention to provide a teeth display container with a clear rotatable cover and with a means of memorializing the loss of a tooth that clearly and directly corresponds to the receptacle in which the particular tooth is stored. The present invention provides all of these features.

Seventh, it is an object of the invention to provide a teeth display container with a clear rotatable cover and having the teeth arranged in the display container in a manner consistent with the teeth's arrangement in the mouth and with a means to indicate a particular tooth to a particular receptacle. The present invention provides all of these features.

Eighth, it is an object of the invention to provide a teeth display container with a clear rotatable cover which also includes a surface in which the display container may be included so as to enlarge and enhance the basal area of the container device. The present invention provides for all of these features.

Ninth, it is an object of the invention to provide a teeth display container with a clear rotatable cover which also has the ability to be framed. The present invention provides for all of these features.

Tenth, it is an object of the invention to provide a teeth display container with a clear rotatable cover which also has the ability to be easily added to an album or three-ring binder. The present invention provides for all of these features.

Eleventh, it is an object of the invention to provide a teeth display container with a clear rotatable cover which is simple. The present invention is very simple to use, as well as convenient and easy to use.

Twelfth, it is an object of the invention to provide a teeth display container with a clear rotatable cover which is inexpensive to manufacture and eliminates parts in the prior art. Prior art devices are complex, with multiple, varied contents all requiring varied systems of manufacture. Additionally, prior art that contains a multiplicity of parts, as well as complicated apparatuses disguised as another item are expensive to manufacture. The present invention eliminates parts in the prior art and is easy and inexpensive to manufacture since the main body is only one molded or formed piece.

Thirteenth, it is an object of the invention to provide a teeth display container with a clear rotatable cover which is inexpensive to purchase. Due to the size, simplicity and uncomplicated nature of the present invention, the present invention will be inexpensive.

Fourteenth, it is an object of the invention to provide a teeth display container with a clear rotatable cover which is age appropriate. Juvenile designs exist in the prior art, but do not take into consideration the young child handling the device, such as turning the device upside down or banging the device on a hard surface. The present invention is able to be turned upside down without loss of any teeth stored in the device and when struck, will not damage nor be damaged by a hard surface. The present invention is age appropriate with a mature design.

Fifteenth, it is an object of the invention to provide a teeth display container with a clear rotatable cover which is durable. Containers or devices to store baby teeth which are made out of cardboard, hard plastic, hard resin, with or without envelopes or pockets are fragile and will not last as long as molded plastic, formed plastic, wood or any other firm, solid material. The present invention is durable.

Sixteenth, it is an object of the invention to provide a teeth display container with a clear rotatable cover which is small and portable. Storage and display devices which are designed to be hung on the wall or which are large and disguised as another item are not portable. Portability offers the advantage of flexibility of placement. The present invention is small and easily portable.

Seventeenth, it is an object of the invention to provide a teeth display container with a clear rotatable cover which is marketable. With the rise in the craft market and in scrap booking, parents have become very active and very creative in creating and saving sentimental memorabilia. The present invention easily lends itself to the craft and scrap booking markets. Marketing slogans and packaging directed at parents, extended family, and friends and the need to save the baby teeth would be very effective and salable. Additionally, there is an endless market for the present invention, as people continue to have children whose teeth will fall out. The present invention is salable, marketable and has an endless, non-seasonable market.

Eighteenth, it is an object of the invention to provide a teeth display container with a clear rotatable cover which is novel. While other patents for storing baby teeth exist, the present invention device has several novel features, one of which is a clear rotatable cover with the inclusion of an aperture that is capable of locking into place. Another novel feature is the closing surface, providing a location for the aperture so that all the receptacles for the teeth are completely covered. Another novel feature is the varied depths of the tooth receptacles so as to provide that all teeth are nearly level with each other and to optimize the viewing and display. Another novel feature is the means of memorialization that directly and clearly relates to each specific tooth. The present invention is unique and novel over other containers.

Nineteenth, it is an object of the invention to provide a teeth display container with a clear rotatable cover which also includes a direct, clear, and easy means to record the loss of the tooth. Prior art has recording methods for tooth storage, but such methods are removable, and thus easily lost, or it is difficult to correlate the recording to the tooth by being in a different location. In addition a viewer has trouble seeing the number system. The present invention includes a recording means that is affixed to the display container and directly corresponds to the tooth memorialized. It is clear and easy for the user to determine where to record the notes for the particular tooth and it is clear and easy for the user to view the recordings and know to which tooth the recording relates. The present invention offers the new feature of direct tooth and recording correlation.

Twentieth, it is an object of the invention to provide a teeth display container with a clear rotatable cover that is appealing and desirable so that someone who sees one demonstrated by another person will want one too. Parents may place the display container in a scrapbook, decorated with the very cute scrap booking additives to permit the book to be demonstrated to friends and family. The design provides access to the teeth to permit the addition of more as the teeth fall out while at the same time does not require deconstruction of the device or the scrapbook page. The same applies if the display container is framed. Children may see these and share with their friends and friends' parents. The friends will want what the other child has and the parents can envisage the very cute and customizable possibilities. The present invention is appealing and desirable.

Twenty-first, it is an object of the invention to provide a teeth display container with a clear rotatable cover that is lightweight and small. Framing, crafting, scrap booking, adding to albums work best when the article to be framed, crafted, added to a scrap book or album is lightweight and small. Furthermore, the small and light weight nature allows the display container to be located anywhere or easily hidden from the child. The present invention is lightweight, small and compact.

Twenty-second, it is an object to provide a teeth display container with a clear rotatable cover which is reliable, reusable, operable, of good quality and useful in its own right. The use of the invention does not depend on others. The quality is high; the product is inexpensive, but not cheap. It is consistent, easy to operate and can be used again and again. The present invention has all of these features.

Twenty-third, it is an object to provide a teeth display container with a viewing means, a recording means, and having the adaptability to be included in a multiplicity of memorabilia devices. The invention can replace all pill bottles, pouches, jewelry boxes, cardboard cards, presently used to store baby teeth and add baby teeth to albums and frames. The present invention fulfills an existing need.

Further novel features and other objects of the present invention will become apparent from the following detailed description, discussion and the appended claims, taken in conjunction with the drawings.

SUMMARY OF THE INVENTION

This invention relates generally to a display/exhibition/showcasing of a collection and more specifically to a repository for the display and exhibiting of deciduous teeth such that all items in the display are capable of being viewed at the same time from a multiplicity of angles, as well as a repository for the permanent storage of deciduous teeth.

The present invention is a simple, lightweight, inexpensive and adaptable display container specifically designed to display all of a baby's teeth from nearly any angle. The invention displays the teeth with respect to each tooth's position in the mouth and has a transparent cover that completely encloses all the teeth and does not need to leave one or two teeth partially uncovered. The present inventions permits the cover to lock in place, either over the cell in which the tooth is placed or over a non-cell surface so that all the cells for the teeth are completely covered and protected. The invention also permits the displayed tooth to be situated close to the underside of the cover to maximize the display of the tooth. The invention permits the baby tooth display to be incorporated into other display devices, such as frames, three-ring binders, scrapbooks, photo albums, and baby albums. It also provides for a mechanism to record or memorialize the events of the tooth that correspond clearly and directly to each tooth.

The present invention comprises the combination of a tooth display allowing all teeth to be viewed simultaneously and in relative order of placement in the mouth, with a dial-like cover that has the ability to resist movement and can completely cover each tooth and not leave any tooth only partially covered, and with tooth receptacles of differing depths so that smaller teeth can be viewed as easily as the larger teeth, and with a means of recording such that the recording device is directly related to a specific tooth, and the entire device is made of a lightweight material that is inexpensive to manufacture, and having the ability to be adaptable to a multiplicity of display formats.

The present invention is a baby tooth album to enable parents to save each baby's tooth and put it in a specific order in a respective pocket associated with each tooth that is indicated by a picture so that the parent knows which tooth came out and where to place it in the baby tooth album. On the back and corresponding to each tooth, there is a space on which parents can write the date that the tooth came out and any other memos and notes to memorialize the occasion, such as the age of the child, what was given to the child in exchange for the tooth or any other reward. The invention has twenty (20) pockets and two (2) closing surfaces with ten (10) pockets arranged on the top half of the baby tooth album and ten (10) pockets arranged on the bottom half of the baby tooth album, which are organized to align with each specific tooth. The invention includes a transparent cover that has one opening with a lip extending along the bottom perimeter of the opening so that the opening will catch on the sidewalls of a pocket with the opening aligned with a pocket to allow a tooth to be inserted. After a tooth has been inserted, the cover can be rotated to a closing surface where, again, the lower lip of the opening will catch on the sides of the closing surface and retain the opening in that position so that the plastic cover will prevent the respective teeth from falling out of the baby tooth album. The cover is affixed to the organizer so that the cover remains over the top of the baby tooth album, and is rotatable over the baby tooth album so that the cover can reposition the opening so that the baby tooth can be properly placed in a specific pocket and thereafter rotated closed. On the back of the baby tooth album, there is a segmented space aligned so that each segment matches each respective pocket so that the date the tooth fell out and other notes can be recorded.

An additional embodiment functions as an album cover which has a fold-over lid that snaps in place onto the corner. The lid has the words "Baby Tooth Album," a number of lines where notes can be written about the child or pictures of the child can be placed. It can also have several plastic sleeves able to contain pictures so that the picture of the baby at the time each time the tooth comes out can also be inserted.

In addition, the baby tooth album can be like a picture that can be placed into a picture frame holder which can then be adapted into a 3-ring binder so that in addition to the child's pictures it can also have all the teeth. The adapter, which is like a sheet of hard paper, has a recess which serves as a locking mechanism so the album can be popped into the adapter. The baby tooth album has the ability to be perforated by a three-hole punch or any other type of punch so that baby tooth album can be placed into a baby album, photo album, scrapbook or alternatively affixed onto another surface.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
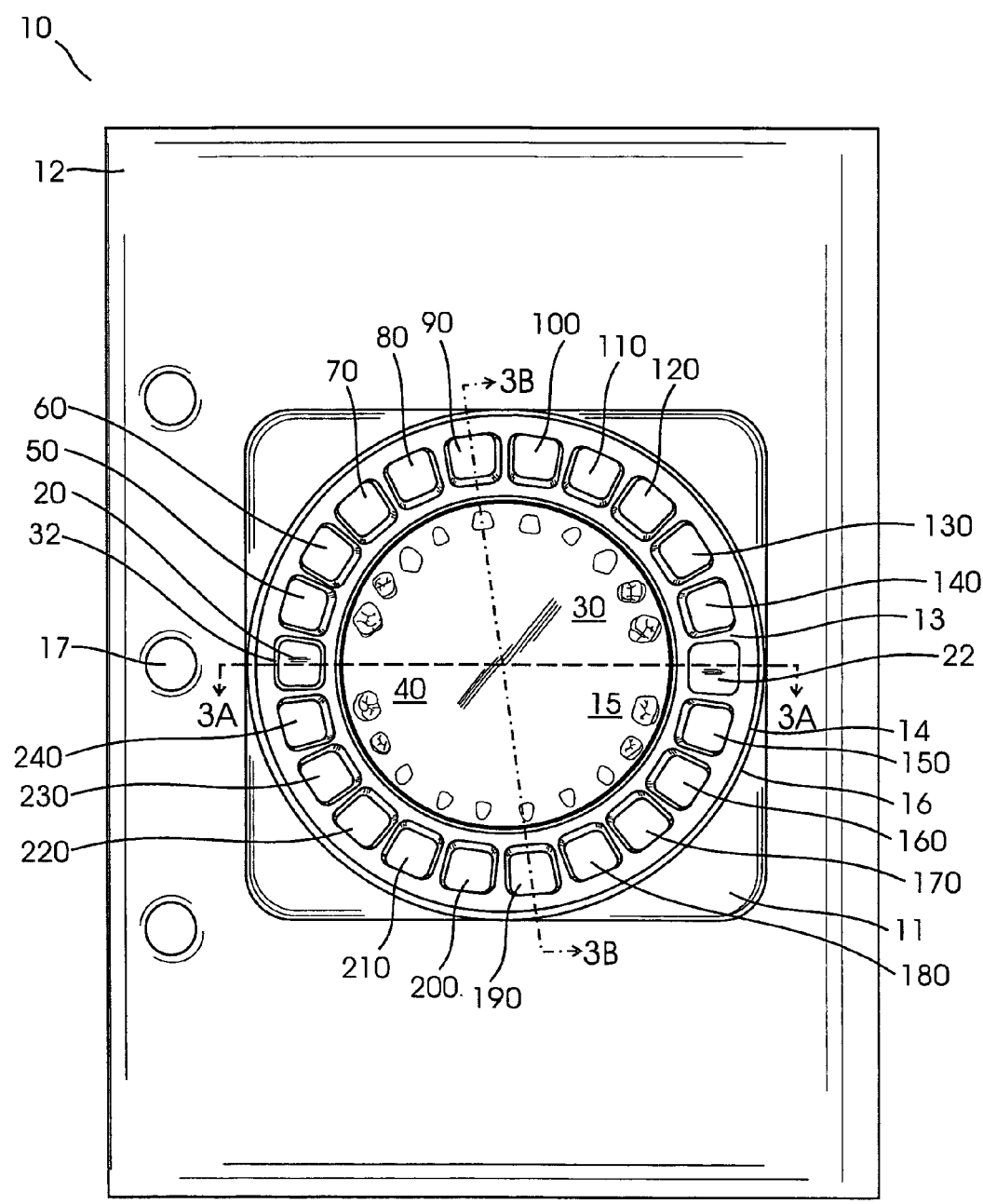
FIG. 1 is a top plan view of a preferred embodiment of the present invention.

Referring to FIG. 1, there is illustrated a top plan view of a preferred embodiment of the present invention. While it may take various configurations, it is preferably shaped as a round, circular disk incorporated into a larger page-like formation. A larger depository album 10 generally made from a firm, yet flexing, polymer material comprises a base 11 having an upwardly ascending riser of 14 which forms into a circular plateau having an outer plateau 13 and an inner plateau 15. The height of the riser 14 thereby establishes the designated height of the raised outer annular plateau 13 in which reside twenty (20) pockets or cells 50, 60, 70, 80, 90, 100, 110, 120, 130, 140, 150, 160, 170, 180, 190, 200, 210, 220, 230, 240 and two (2) closing surfaces 20, 22 and from which an inner plateau 15 extends from outer annular plateau 13 after a slight descent to encompass the entirety of the center of outer annular plateau 13. In a preferred embodiment, base 11 is in combination with integrative surface 12 which has a multiplicity of advantages including the ability to frame depository album 10, and the ability to add depository album 10 to a three ring binder or any other binder such as a scrap book or baby album by means of adding the required number of holes 17 to the integrative surface 12.

Encompassing that portion of the depository album 10 circumscribed by the upwardly ascending riser 14 is a rotatable transparent cover 30 having one (1) aperture 32 through which a tooth is submitted into a particular cell 50, 60, 70, 80, 90, 100, 110, 120, 130, 140, 150, 160, 170, 180, 190, 200, 210, 220, 230, 240 by passing through aperture 32 then cell ingress 50a, 60a, 70a, 80a, 90a, 100a, 110a, 120a, 130a, 140a, 150a, 160a, 170a, 180a, 190a, 200a, 210a, 220a, 230a, 240a to rest upon cell base 50b, 60b, 70b, 80b, 90b, 100b, 110b, 120b, 130b, 140b, 150b, 160b, 170b, 180b, 190b, 200b, 210b, 220b, 230b, 240b and also preventing any other teeth residing in depository album 10 from leaving its cell 50, 60, 70, 80, 90, 100, 110, 120, 130, 140, 150, 160, 170, 180, 190, 200, 210, 220, 230, 240.

The rotatable transparent cover 30 is held in place by shaping itself along the riser of outer annular plateau 14 by skimming vertically down the riser of outer annular plateau 14 from the top rim of the outer annular plateau 13 to the base 12, over the rib 16 on the riser of outer annular plateau 14 and skimming down the remainder of the riser of outer annular plateau 14.

Flange 34 extends downwardly from the entire perimeter of the aperture 32, thereby enabling aperture 32 to be "locked" in place over the chosen cell ingress 50a, 60a, 70a, 80a, 90a, 100a, 110a, 120a, 130a, 140a, 150a, 160a, 170a, 180a, 190a, 200a, 210a, 220a, 230a, 240a as determined by manual manipulation of rotatable transparent cover 30 by means of extending into the cell 50, 60, 70, 80, 90, 100, 110, 120, 130, 140, 150, 160, 170, 180, 190, 200, 210, 220, 230, 240 and inhibited in movement by surrounding walls 50c, 60c, 70c, 80c, 90c, 100c, 110c, 120c, 130c, 140c, 150c, 160c, 170c, 180c, 190c, 200c, 210c, 220c, 230c, 240c, but not inhibited to the extent that with minor exertion rotatable transparent cover 30 can be again rotated to place aperture 32 over another cell 50, 60, 70, 80, 90, 100, 110, 120, 130, 140, 150, 160, 170, 180, 190, 200, 210, 220, 230, 240 or placed over left closing surface 20 or right closing surface 22. Flange 34 also allows aperture 32 to be "locked" in place over left closing surface 20 or right closing surface 22 by means of left closing surface 20 and right closing surface 22 having a face 20a, 22a being a level depression whose descension 20b, 22b from outer annular plateau 13 is at least equal to the length of flange 34 and having a perimeter such that the entirety of aperture 32 can reside within left closing surface 20 or right closing surface 22 and thereby creating resistance so that aperture 32 is inhibited from moving from left closing surface 20 or right closing surface 22. This is to ensure that no cell 50, 60, 70, 80, 90, 100, 110, 120, 130, 140, 150, 160, 170, 180, 190, 200, 210, 220, 230, 240 is left with aperture 32 remaining over it except by choice, to prevent aperture 32 from sliding to a cell 50, 60, 70, 80, 90, 100, 110, 120, 130, 140, 150, 160, 170, 180, 190, 200, 210, 220, 230, 240 and enabling a tooth to escape, and to prevent dust and other particles and matter from entering the cell 50, 60, 70, 80, 90, 100, 110, 120, 130, 140, 150, 160, 170, 180, 190, 200, 210, 220, 230, 240 thereby preventing the damaging, deteriorating or dirtying of the tooth. The advantages of having two (2) closing surfaces 20, 22 opposite each other on the outer annular plateau 13 are that manual manipulation of aperture 32 to left closing surface 20 or right closing surface 22, requires no more than a one hundred eight (180) degree rotation of rotatable transparent cover 30 to place aperture 32 over left closing surface 20 or right closing surface 22 and that placement of the left closing surface 20 and right closing surface 22 opposite each other horizontally between cell 240 and cell 50 and between cell 140 and cell 150 enhances the visual aspect of separating the teeth of the upper jaw from the teeth of the lower jaw, as well as aiding in the placement of the tooth in the appropriate cell 50, 60, 70, 80, 90, 100, 110, 120, 130, 140, 150, 160, 170, 180, 190, 200, 210, 220, 230, 240.

Adhered to and situated on the inner plateau 15 to be seen from under the rotatable transparent cover 30 is a customizable label and tooth indicia 40 that displays a picture of each of the twenty (20) baby teeth in the order each tooth is located in the mouth, with the teeth of the upper jaw pictured and listed along the upper hemisphere of customizable label and tooth indicia 40 following the curve of the upper hemisphere of customizable label and tooth indicia 40 and the teeth of the lower jaw pictured and listed along the lower hemisphere of customizable label and tooth indicia 40 and following along the curve of customizable label and tooth indicia 40. The customizable label and tooth indicia 40 is oriented on the inner plateau 15 so that the picture of each tooth is aligned to the appropriate cell 50, 60, 70, 80, 90, 100, 110, 120, 130, 140, 150, 160, 170, 180, 190, 200, 210, 220, 230, 240.

Each cell 50, 60, 70, 80, 90, 100, 110, 120, 130, 140, 150, 160, 170, 180, 190, 200, 210, 220, 230, 240 is comprised of a base 50b, 60b, 70b, 80b, 90b, 100b, 110b, 120b, 130b, 140b, 150b, 160b, 170b, 180b, 190b, 200b, 210b, 220b, 230b, 240b opposite the cell ingress 50a, 60a, 70a, 80a, 90a, 100a, 110a, 120a, 130a, 140a, 150a, 160a, 170a, 180a, 190a, 200a, 210a, 220a, 230a, 240a and surrounding walls 50c, 60c, 70c, 80c, 90c, 100c, 110c, 120c, 130c, 140c, 150c, 160c, 170c, 180c, 190c, 200c, 210c, 220c, 230c, 240c delineating the perimeter of base 50b, 60b, 70b, 80b, 90b, 100b, 110b, 120b, 130b, 140b, 150b, 160b, 170b, 180b, 190b, 200b, 210b, 220b, 230b, 240b. Surrounding walls 50c, 60c, 70c, 80c, 90c, 100c, 110c, 120c, 130c, 140c, 150c, 160c, 170c, 180c, 190c, 200c, 210c, 220c, 230c, 240c are comprised of an outer side 50d, 60d, 70d, 80d, 90d, 100d, 110d, 120d, 130d, 140d, 150d, 160d, 170d, 180d, 190d, 200d, 210d, 220d, 230d, 240d, a right side 50e, 60e, 70e, 80e, 90e, 100e, 110e, 120e, 130e, 140e, 150e, 160e, 170e, 180e, 190e, 200e, 210e, 220e, 230e, 240e, an inner side 50f, 60f, 70f, 80f, 90f, 100f, 110f, 120f, 130f, 140f, 150f, 160f, 170f, 180f, 190f, 200f, 210f, 220f, 230f, 240f and a left side 50g, 60g, 70g, 80g, 90g, 100g, 110g, 120g, 130g, 140g, 150g, 160g, 170g, 180g, 190g, 200g, 210g, 220g, 230g, 240g.

The depth of each cell 50, 60, 70, 80, 90, 100, 110, 120, 130, 140, 150, 160, 170, 180, 190, 200, 210, 220, 230, 240 is determined by the length of each cell's 50, 60, 70, 80, 90, 100, 110, 120, 130, 140, 150, 160, 170, 180, 190, 200, 210, 220, 230, 240 surrounding walls 50c, 60c, 70c, 80c, 90c, 100c, 110c, 120c, 130c, 140c, 150c, 160c, 170c, 180c, 190c, 200c, 210c, 220c, 230c, 240c such that each tooth will lie as closely to the ingress of the cell 50a, 60a, 70a, 80a, 90a, 100a, 110a, 120a, 130a, 140a, 150a, 160a, 170a, 180a, 190a, 200a, 210a, 220a, 230a, 240a but below the level of the rotatable transparent cover 30 so that each tooth in each cell 50, 60, 70, 80, 90, 100, 110, 120, 130, 140, 150, 160, 170, 180, 190, 200, 210, 220, 230, 240 is easily visible and viewable, yet not impeding movement of rotatable transparent cover 30.

Figure 2:
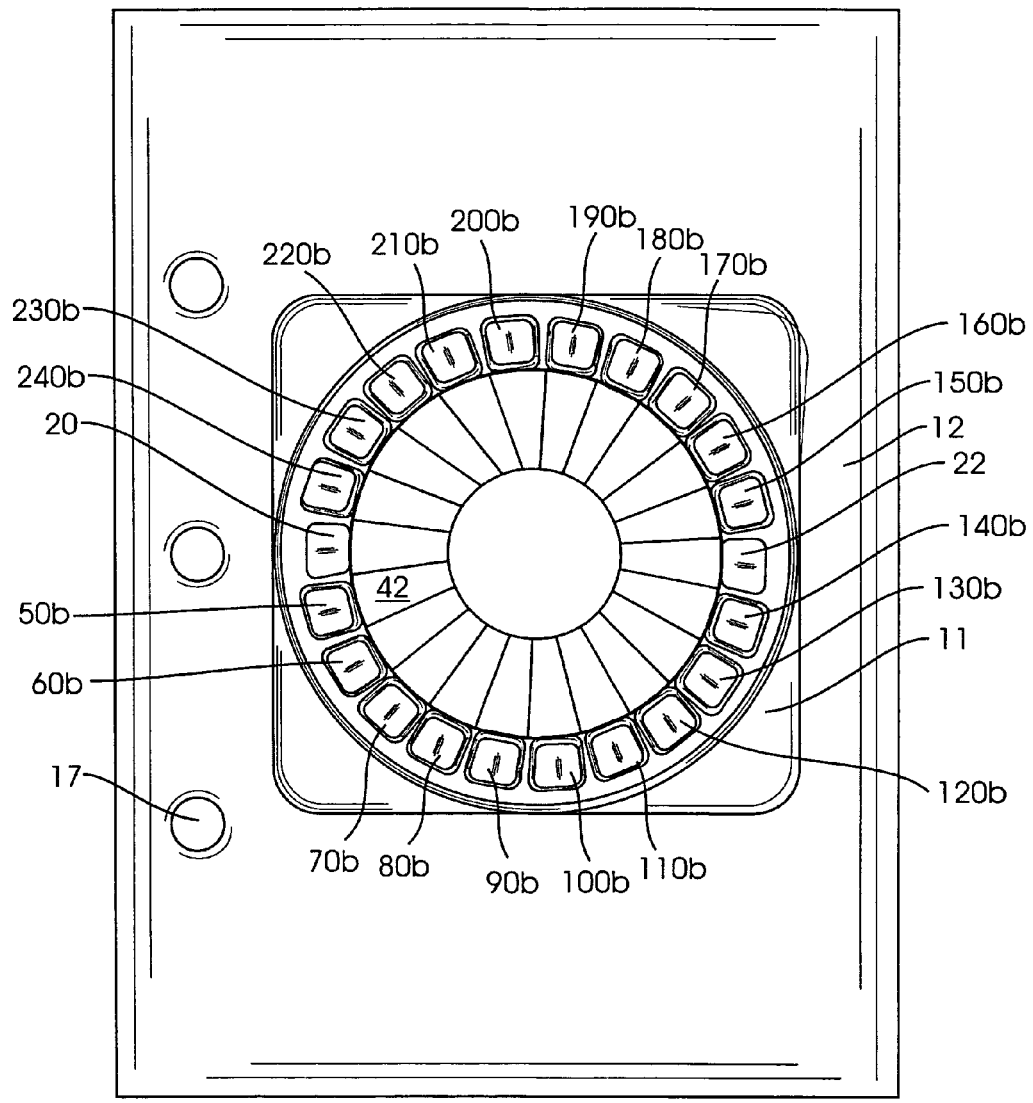
FIG. 2 is a bottom plan of the preferred embodiment of the present invention illustrated in FIG. 1.

Referring to FIG. 2, there is shown a bottom plan view of the preferred embodiment of depository album 10 comprising base 11 on an integrative surface 12. The depository album 10, being a non-solid structure, has an underside on the reverse, which is in relief to the upper surface of depository album 10. The reverse of inner plateau 15 has affixed to it a personalizable label 42 that has markings that segment the personalizable label 42 into sections that correspond to and are aligned with each cell 50, 60, 70, 80, 90, 100, 110, 120, 130, 140, 150, 160, 170, 180, 190, 200, 210, 220, 230, 240 and upon which recordations regarding each tooth may be memorialized.

When, as in the preferred embodiment, the base 11 is a part of the integrative surface 12 the bottom of the depository album 10 is in full view and easily accessible.

Figure 3A:
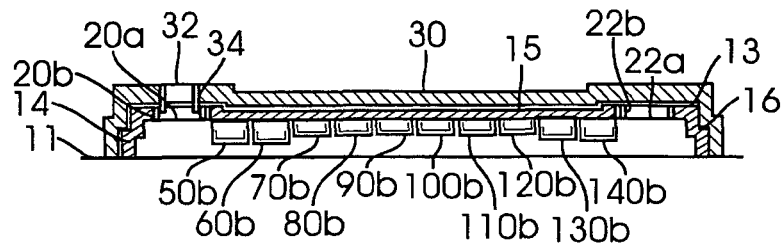
FIG. 3A is a vertical cross sectional detailed view of the depository album present invention taken along line 3A-3A of FIG. 1 showing the aperture and flange of the rotating cover over the left closing surface and in relation to the right closing surface and other cells.

Referring to FIG. 3A, the illustration shows a vertical cross section detail view of depository album 10 showing the rotatable transparent cover 30 aperture 32, and flange 34 in relation to riser of outer annular plateau 14, forming into outer annular plateau 13, left closing surface 20, descension of left closing surface 20b, face of left closing surface 20a, inner plateau 15, right closing surface 22, descension of right closing surface 22b, and face of right closing surface 22a.

When rotatable transparent cover 30 is rotated to position aperture 32 over a closing surface 20, 22, flange 34 extends downwards from aperture 32 to below upper perimeter of closing surface descension 20b, 22b and lie within the bounds of descension 20b, 22b of closing surface 20, 22. Movement of rotatable transparent cover 30 is constrained by flange's 34 extension downwards from perimeter of aperture 32 into closing surface 20, 22. Movement of rotatable transparent cover 30 is further restricted by the proximity of flange 34 to descension 20b, 22b. The closeness of flange 34 to closing surface descension 20b, 22b prevents the rotatable transparent cover from freely moving from designated closing surface 20, 22 and also restricts the freedom of movement of aperture 32 over closing surface 20, 22 by holding aperture 32 over closing surface 20, 22 so that any quivering of aperture 32 over closing surface 20, 22 is kept to a minimum, if not prohibited.

Figure 3B:
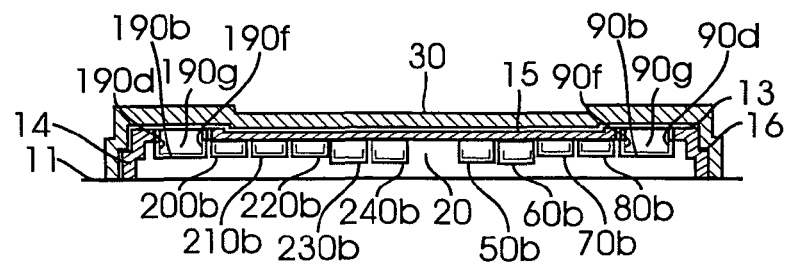
FIG. 3B is a vertical cross sectional detailed view of the depository album present invention taken along line 3A-3A of FIG. 1 showing the rotating cover covering at least two of the cells and in relation to other cells.
Figure 3C:
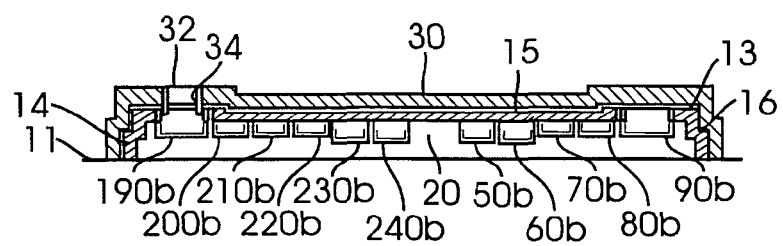
FIG. 3C is an imaginary, vertical cross sectional detailed view of the depository album present invention, wherein the cover has been rotated so as to show the aperture and flange of the rotating cover over a cell and in relation to the other cells.

Referring to FIGS. 3B and 3C, there is shown a vertical cross sectional detail view of depository album 10 showing the rotatable transparent cover 30 aperture 32, and flange 34 in relation to riser of outer annular plateau 14, forming into outer annular plateau 13, and either left closing surface 20 or right closing surface 22 or cell ingress 50a, 60a, 70a, 80a, 90a, 100a, 110a, 120a, 130a, 140a, 150a, 160a, 170a, 180a, 190a, 200a, 210a, 220a, 230a, 240a, and surrounding walls 50c, 60c, 70c, 80c, 90c, 100c, 110c, 120c, 130c, 140c, 150c, 160c, 170c, 180c, 190c, 200c, 210c, 220c, 230c, 240c, and inner plateau 15.

In relation to cells 50, 60, 70, 80, 90, 100, 110, 120, 130, 140, 150, 160, 170, 180, 190, 200, 210, 220, 230, 240:

When rotatable transparent cover 30 is rotated to position aperture 32 over a cell 50, 60, 70, 80, 90, 100, 110, 120, 130, 140, 150, 160, 170, 180, 190, 200, 210, 220, 230, 240, flange 34 extends downwards from aperture 32 to below perimeter of cell ingress 50a, 60a, 70a, 80a, 90a, 100a, 110a, 120a, 130a, 140a, 150a, 160a, 170a, 180a, 190a, 200a, 210a, 220a, 230a, 240a and lie within the surrounding walls 50c, 60c, 70c, 80c, 90c, 100c, 110c, 120c, 130c, 140c, 150c, 160c, 170c, 180c, 190c, 200c, 210c, 220c, 230c, 240c of cells 50, 60, 70, 80, 90, 100, 110, 120, 130, 140, 150, 160, 170, 180, 190, 200, 210, 220, 230, 240. Movement of rotatable transparent cover 30 is constrained by flange's 34 extension downwards from perimeter of aperture 32 into cell 50, 60, 70, 80, 90, 100, 110, 120, 130, 140, 150, 160, 170, 180, 190, 200, 210, 220, 230, 240. Movement of rotatable transparent cover 30 is further restricted by the proximity of flange 34 to surrounding walls 50c, 60c, 70c, 80c, 90c, 100c, 110c, 120c, 130c, 140c, 150c, 160c, 170c, 180c, 190c, 200c, 210c, 220c, 230c, 240c. The closeness of flange 34 to surrounding walls 50c, 60c, 70c, 80c, 90c, 100c, 110c, 120c, 130c, 140c, 150c, 160c, 170c, 180c, 190c, 200c, 210c, 220c, 230c, 240c, prevents rotatable transparent cover from freely moving from designated cell 50, 60, 70, 80, 90, 100, 110, 120, 130, 140, 150, 160, 170, 180, 190, 200, 210, 220, 230, 240 and also restricts the freedom of movement of aperture 32 over cell 50, 60, 70, 80, 90, 100, 110, 120, 130, 140, 150, 160, 170, 180, 190, 200, 210, 220, 230, 240 by holding aperture 32 over cell ingress 50a, 60a, 70a, 80a, 90a, 100a, 110a, 120a, 130a, 140a, 150a, 160a, 170a, 180a, 190a, 200a, 210a, 220a, 230a, 240a so that any quivering of aperture 32 over cell 50, 60, 70, 80, 90, 100, 110, 120, 130, 140, 150, 160, 170, 180, 190, 200, 210, 220, 230, 240 and cell ingress 50a, 60a, 70a, 80a, 90a, 100a, 110a, 120a, 130a, 140a, 150a, 160a, 170a, 180a, 190a, 200a, 210a, 220a, 230a, 240a is kept to a minimum, if not prohibited.

Figure 3D:
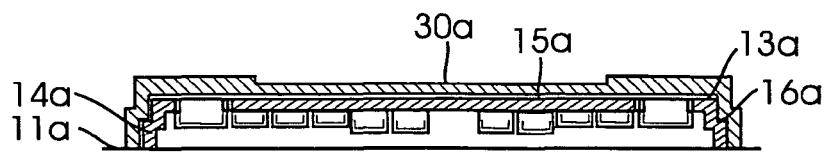
FIG. 3D is a vertical cross sectional detailed view of an alternative embodiment of the depository album present invention showing a view similar to that in FIG. 3B, wherein the inner plateau has a surface that is level with the outer annular plateau.

Referring to FIG. 3D, there is shown an alternate embodiment of the present invention wherein the inner plateau 15a is level with the outer annular plateau 13a.

Figure 4:
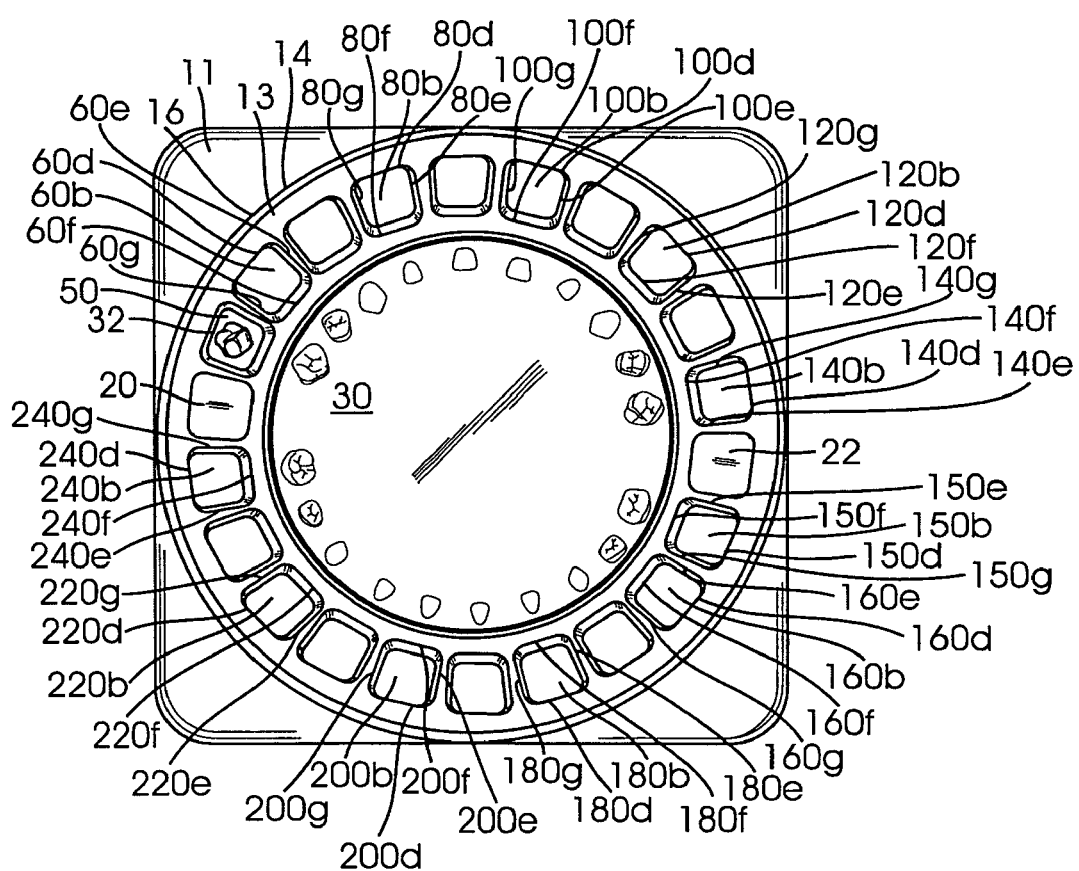
FIG. 4 is a close up, top plan view of the depository album present invention showing a tooth in a cell over which the aperture of the cover is aligned in accordance with one aspect of the invention.

Referring to FIG. 4, there is shown a top plan view of the depository album 10 from base 11 showing a tooth in a cell 50, 60, 70, 80, 90, 100, 110, 120, 130, 140, 150, 160, 170, 180, 190, 200, 210, 220, 230, 240, specifically the cell for upper right second molar 50, with aperture 34 of the rotatable transparent cover 30 aligned over cell 50, 60, 70, 80, 90, 100, 110, 120, 130, 140, 150, 160, 170, 180, 190, 200, 210, 220, 230, 240 so as to permit the deposit of a tooth through aperture 32 and cell ingress 50a, 60a, 70a, 80a, 90a, 100a, 110a, 120a, 130a, 140a, 150a, 160a, 170a, 180a, 190a, 200a, 210a, 220a, 230a, 240a to rest upon cell base 50b, 60b, 70b, 80b, 90b, 100b, 110b, 120b, 130b, 140b, 150b, 160b, 170b, 180b, 190b, 200b, 210b, 220b, 230b, 240b, whose height, as determined by surrounding walls 50c, 60c, 70c, 80c, 90c, 100c, 110c, 120c, 130c, 140c, 150c, 160c, 170c, 180c, 190c, 200c, 210c, 220c, 230c, 240c, is in relation to the height and size of the tooth, so as to bring the top of the tooth as nearly to yet still below the cell ingress 50a, 60a, 70a, 80a, 90a, 100a, 110a, 120a, 130a, 140a, 150a, 160a, 170a, 180a, 190a, 200a, 210a, 220a, 230a, 240a so as not to impede the movement of rotatable transparent cover 30 and to optimize the viewing of the tooth through rotatable transparent cover 30.

It is also shown in FIG. 4. that tooth in cell 50, 60, 70, 80, 90, 100, 110, 120, 130, 140, 150, 160, 170, 180, 190, 200, 210, 220, 230, 240, specifically cell 50, correlates to the tooth pictured on customizable label and tooth indicia 40 for the individual cell 50, 60, 70, 80, 90, 100, 110, 120, 130, 140, 150, 160, 170, 180, 190, 200, 210, 220, 230, 240, thereby aiding the correct placement of the tooth in depository album 10 and educationally in relation to the other teeth in the mouth.

Figure 5:
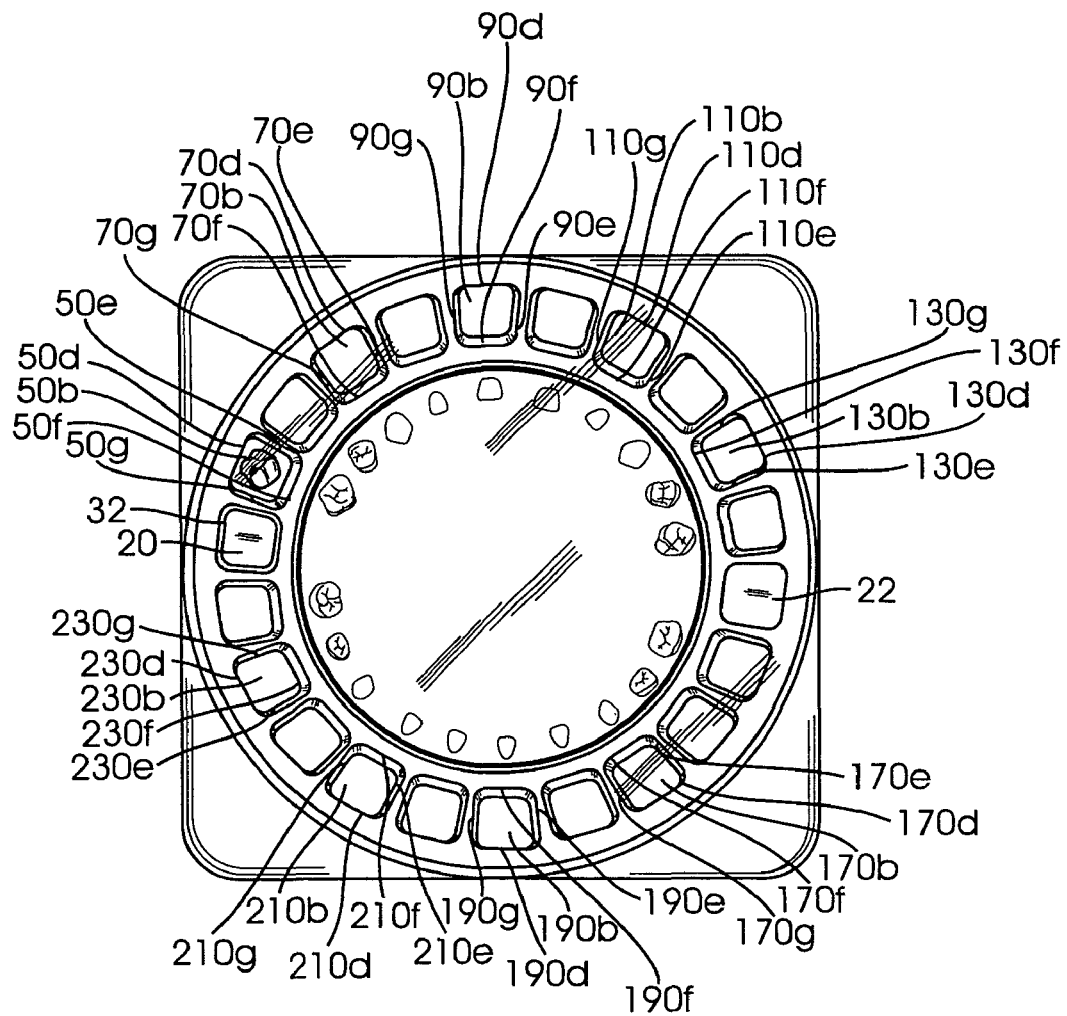
FIG. 5 is a close up, top plan view of the depository album present invention showing a tooth in a cell with the aperture of the cover in the closed position in accordance with one aspect of the invention.

Referring to FIG. 5, there is illustrated a top plan view of the depository album 10 showing a tooth in a cell 50, 60, 70, 80, 90, 100, 110, 120, 130, 140, 150, 160, 170, 180, 190, 200, 210, 220, 230, 240, specifically cell 50, with aperture 32 of the rotatable transparent cover 30 over closing surface 20, 22 specifically [left/right] closing surface [20, 22] and thus 'locked' in a closed position over closing surface 20, 22, as discussed in FIG. 1 and FIG. 3.

The inclusion of a closing surface 20, 22 is most advantageous and serves a plurality of purposes which are lacking in the prior art. As discussed in FIGS. 1, 3 and 4, the closing surface 20, 22 allows the aperture 34 to be in a position that is not over a cell 50, 60, 70, 80, 90, 100, 110, 120, 130, 140, 150, 160, 170, 180, 190, 200, 210, 220, 230, 240 and therefore prevents a tooth from escaping the cell 50, 60, 70, 80, 90, 100, 110, 120, 130, 140, 150, 160, 170, 180, 190, 200, 210, 220, 230, 240 through the aperture 34 particularly when the depository album is turned over to view or write on personalizable label 42 on the reverse of the depository album 10.

Another advantage of the inclusion of a closing surface 20, 22 is that when depository album 10 is kept in the closed position aperture 32 over closing surface 20, 22 each and everyone of the cells 50, 60, 70, 80, 90, 100, 110, 120, 130, 140, 150, 160, 170, 180, 190, 200, 210, 220, 230, 240 has its ingress 50a, 60a, 70a, 80a, 90a, 100a, 110a, 120a, 130a, 140a, 150a, 160a, 170a, 180a, 190a, 200a, 210a, 220a, 230a, 240a protected from the outside world by the rotatable transparent cover 30 so as to prevent the entrance of dust, dirt and other particles and matters that may otherwise enter the cells 50, 60, 70, 80, 90, 100, 110, 120, 130, 140, 150, 160, 170, 180, 190, 200, 210, 220, 230, 240 and have the undesired effect of dirtying the cell 50, 60, 70, 80, 90, 100, 110, 120, 130, 140, 150, 160, 170, 180, 190, 200, 210, 220, 230, 240, as well as dirtying or damaging the tooth.

A further advantage of the inclusion of a closing surface 20, 22 is that the rotatable transparent cover 30 is locked closed when aperture 32 is in position over closing surface 20, 22. The ability to lock closed has the additional advantage of granting consumers a confidence that the depository album 10, if shifted, moved or pressed upon, such as in an album, will not accidently turn rotatable transparent cover 30 so that aperture 32 is not displaced from closing surface 20, 22 to a cell 50, 60, 70, 80, 90, 100, 110, 120, 130, 140, 150, 160, 170, 180, 190, 200, 210, 220, 230, 240, which would allow particulates to enter and a tooth to exit.

The locking ability of depository album 10 further grants confidence to allow a child to hold and view the depository album 10 without fear that the child will let loose a tooth from depository album 10. A young child may turn the depository album 10 upside down and still a tooth will not exit if the aperture 32 is over a closing surface 20, 22.

Figure 6:
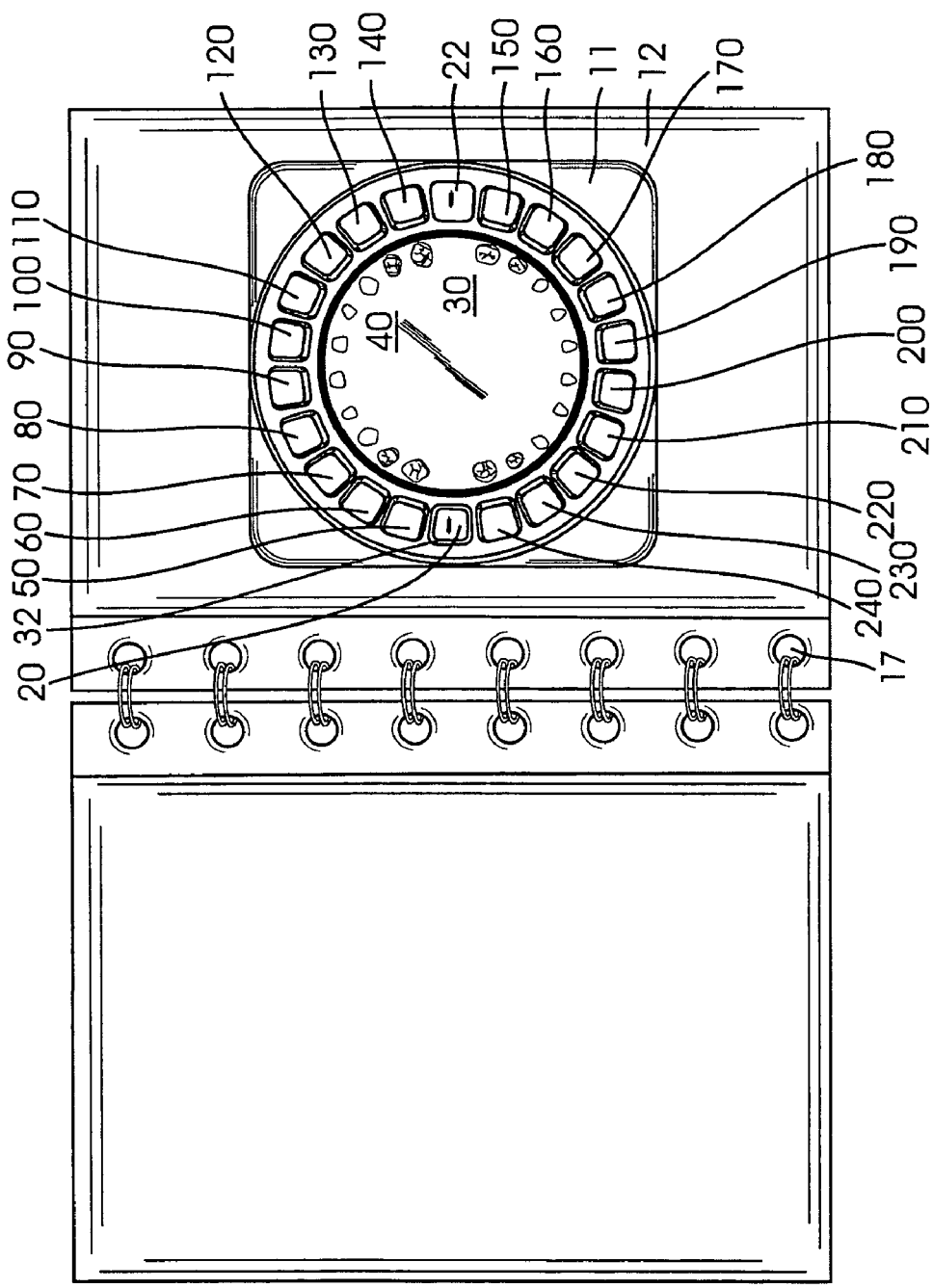
FIG. 6 is a top plan view of the depository album present invention from FIG. 1 shown as adaptable to a photo album or scrap book in accordance with one aspect of the invention.

Referring to FIG. 6, there is shown a top plan view of the depository album 10 shown fully on the integrative surface 12 and showing the personalization and adaptability available to add additions such as one or more holes 17 to the depository album 10 so as to adapt the depository album 10 to be part of a photo album or scrap book.

Figure 7:
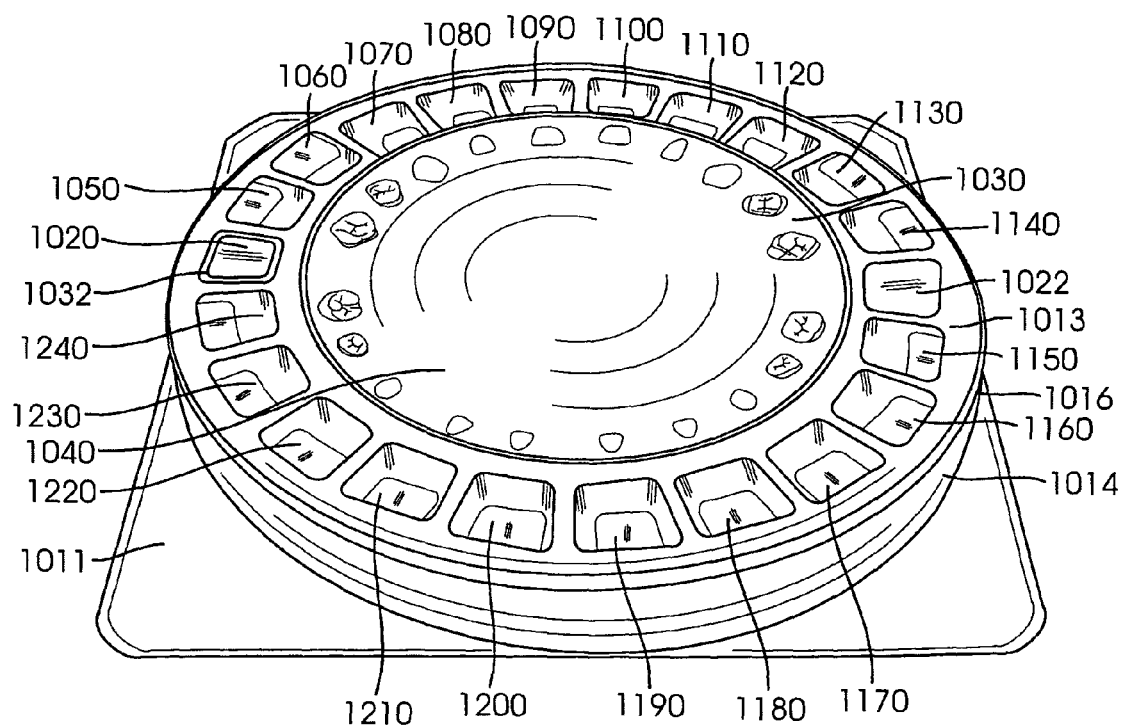
FIG. 7 is a top perspective view of an alternate embodiment of the depository album invention in accordance with one aspect of the invention.

Referring to FIG. 7, there is shown a top perspective view of an alternative embodiment of the present invention depository album 1010 as described in FIG. 1 without an integrative surface 1012 and being a free standing device.

Figure 8:
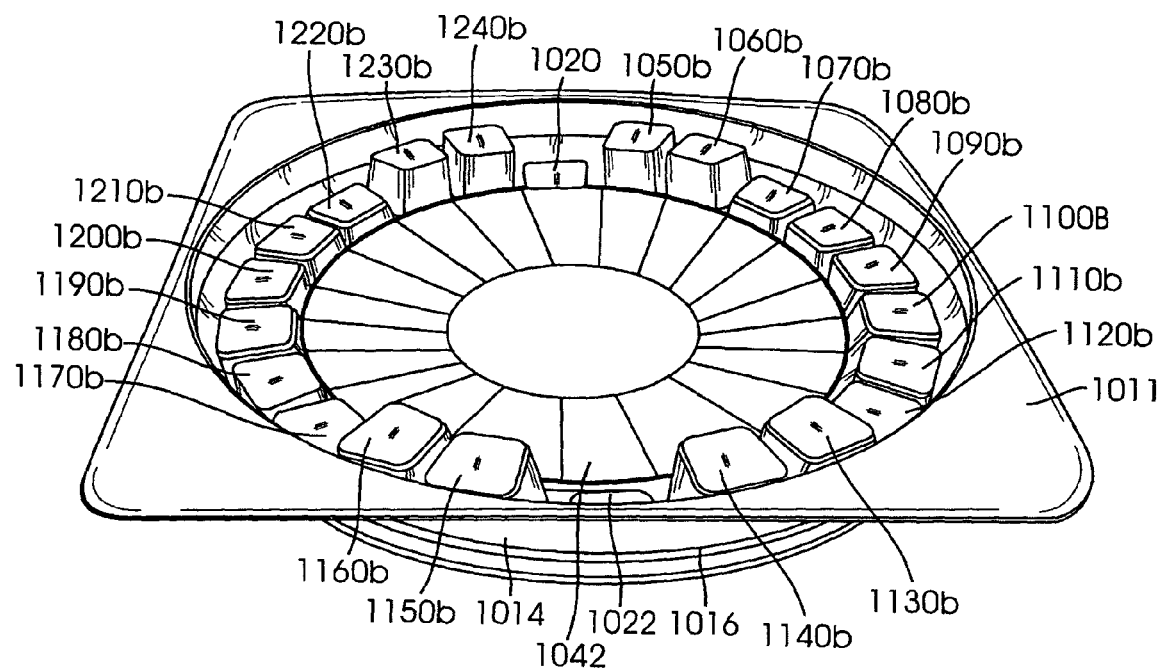
FIG. 8 is a bottom plan perspective view of an alternate embodiment of the depository album present invention in accordance with one aspect of the invention.

Referring to FIG. 8, there is shown a bottom perspective view of the alternative embodiment of the depository album 1010 shown in FIG. 7 without being integrated into an integrative surface 1012 and just being a free standing device. FIG. 8 illustrates the different sizes and lengths of surrounding walls 1050c, 1060c, 1070c, 1080c, 1090c, 1100c, 1110c, 1120c, 1130c, 1140c, 1150c, 1160c, 1170c, 1180c, 1190c, 1200c, 1210c, 1220c, 1230c, 1240c of each cell 1050, 1060, 1070, 1080, 1090, 1100, 1110, 1120, 1130, 1140, 1150, 1160, 1170, 1180, 1190, 1200, 1210, 1220, 1230, 1240. FIG. 8 further illustrates that the depth of each cell 1050, 1060, 1070, 1080, 1090, 1100, 1110, 1120, 1130, 1140, 1150, 1160, 1170, 1180, 1190, 1200, 1210, 1220, 1230, 1240 does not extend beyond the base 1011. This allows the depository album 1010 to lie within and be part of an album by lying flat on the page or leaf behind it. FIG. 8 also shows that the orientation of personalizable label 1042 places each segment with a particular cell 1050, 1060, 1070, 1080, 1090, 1100, 1110, 1120, 1130, 1140, 1150, 1160, 1170, 1180, 1190, 1200, 1210, 1220, 1230, 1240. This has the advantage of allowing a viewer to directly correlate the recorded data with the tooth in question.

Figure 9:
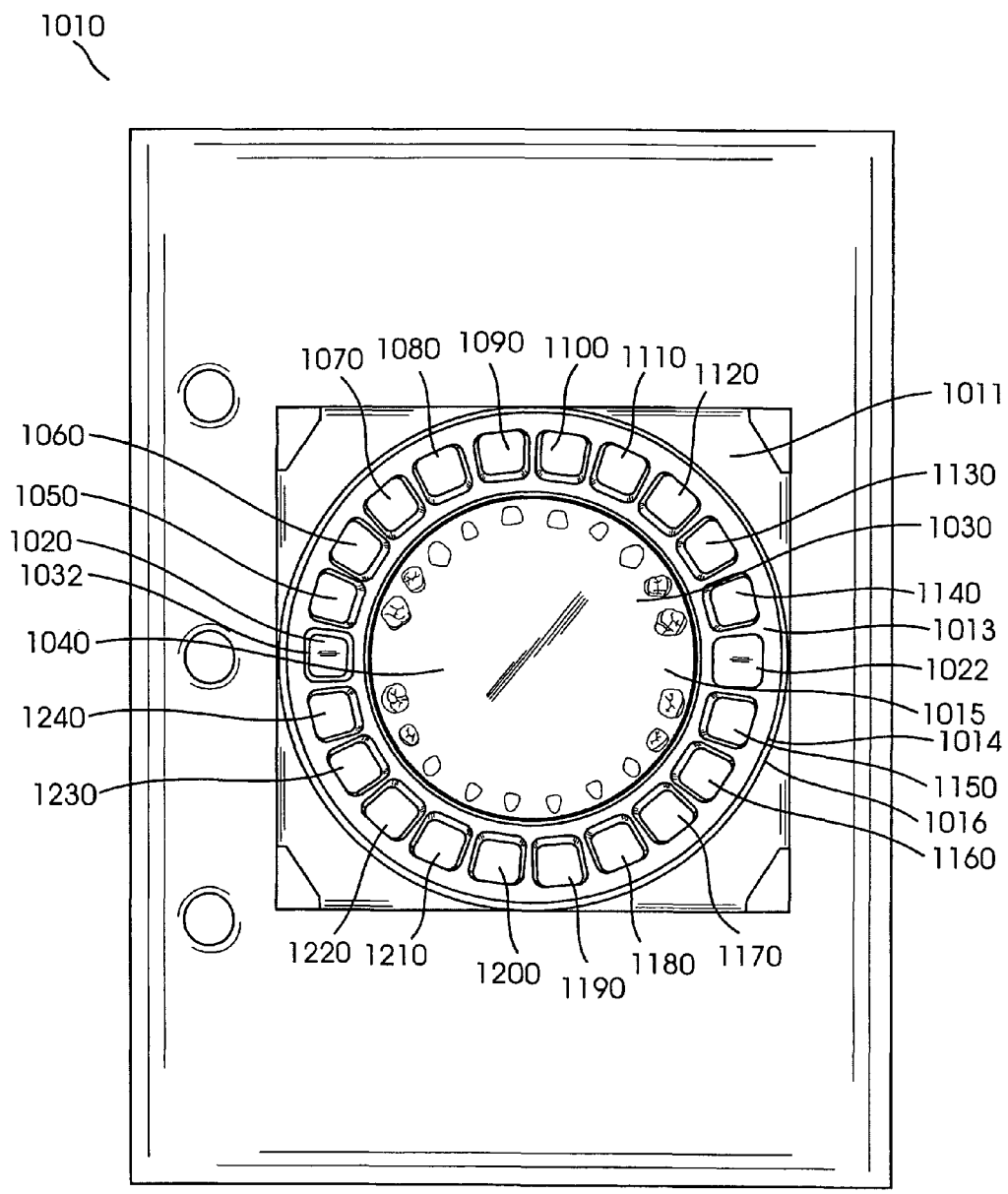
FIG. 9 is a top plan view of an alternative embodiment of the present invention in which the depository album is capable of being adhered to an album, scrapbook or picture frame, and is adhered to a page designed for a three-ring binder.

Referring to FIG. 9, there is illustrated a top plan view of the alternate embodiment of the present invention being mounted on a page. While it may take various configurations, it is preferably shaped as a round, circular disk with a flat protrusion extending from the bottom perimeter of the base and expanding out in the same plane as the underside of the circular disk. A larger depository album 1010 generally made from a firm, yet flexing, polymer material comprises a base 1011 having an upwardly riser 1014 which forms into a circular plateau having an outer plateau 1013 and an inner plateau 1015. The height of the riser 1014 thereby establishes the designated height of the raised outer annular plateau 1013 in which reside twenty (20) pockets or cells 1050, 1060, 1070, 1080, 1090, 1100, 1110, 1120, 1130, 1140, 1150, 1160, 1170, 1180, 1190, 1200, 1210, 1220, 1230, 1240 and two (2) closing surfaces 1020, 1022, and from which an inner plateau 1015 extends from outer annular plateau 1013 after a slight descent to encompass the entirety of the center of outer annular plateau 1013.

Base 1011 has sides, bottom and corners that are compatible with installation of the depository album 1010 onto another surface by a multiplicity of methods including, as pictured here, by means of common corner adhesives so as to adhere the alternate embodiment of the depository album 1010 onto a leaf of an album or scrap book. The lightweight nature of the depository album 1010 allows for optimal flexibility in the displaying and decorating of the depository album 1010.

Encompassing that portion of the depository album 1010 circumscribed by the upwardly ascending riser of outer annular plateau 1014 is a rotatable transparent cover 1030 having one (1) aperture 1032 through which a tooth is submitted into a particular cell 1050, 1060, 1070, 1080, 1090, 1100, 1110, 1120, 1130, 1140, 1150, 1160, 1170, 1180, 1190, 1200, 1210, 1220, 1230, 1240 by passing through aperture 1032 then cell ingress 1050a, 1060a, 1070a, 1080a, 1090a, 1100a, 1110a, 1120a, 1130a, 1140a, 1150a, 1160a, 1170a, 1180a, 1190a, 1200a, 1210a, 1220a, 1230a, 1240a to rest upon cell base 1050b, 1060b, 1070b, 1080b, 1090b, 1100b, 1110b, 1120b, 1130b, 1140b, 1150b, 1160b, 1170b, 1180b, 1190b, 1200b, 1210b, 1220b, 1230b, 1240b and also preventing any other teeth residing in depository album 1010 from leaving its cell 1050, 1060, 1070, 1080, 1090, 1100, 1110, 1120, 1130, 1140, 1150, 1160, 1170, 1180, 1190, 1200, 1210, 1220, 1230, 1240.

The rotatable transparent cover 1030 is held in place by shaping itself along the riser of outer annular plateau 1014 by skimming vertically down the riser of outer annular plateau 1014 from the top rim of the outer annular plateau 1013 to the base 1011, over the rib 1016 on the riser of outer annular plateau 1014 and skimming down the remainder of the riser of outer annular plateau 1014.

Flange 1034 extends downwardly from the entire perimeter of the aperture 1032, thereby enabling aperture 1032 to be "locked" in place over the chosen cell ingress 1050a, 1060a, 1070a, 1080a, 1090a, 1100a, 1110a, 1120a, 1130a, 1140a, 1150a, 1160a, 1170a, 1180a, 1190a, 1200a, 1210a, 1220a, 1230a, 1240a as determined by manual manipulation of rotatable transparent cover 1030 by means of extending into the cell 1050, 1060, 1070, 11080, 1090, 1100, 1110, 1120, 1130, 1140, 1150, 1160, 1170, 1180, 1190, 1200, 1210, 1220, 1230, 1240 and inhibited in movement by surrounding walls 1050c, 1060c, 1070c, 1080c, 1090c, 1100c, 1110c, 1120c, 1130c, 1140c, 1150c, 1160c, 1170c, 1180c, 1190c, 1200c, 1210c, 1220c, 1230c, 1240c, but not inhibited to the extent that with minor exertion rotatable transparent cover 1030 can be again rotated to place aperture 1032 over another cell 1050, 1060, 1070, 1080, 1090, 1100, 1110, 1120, 1130, 1140, 1150, 1160, 1170, 1180, 1190, 1200, 1210, 1220, 1230, 1240 or placed over left closing surface 1020 or right closing surface 1022. Flange 1034 also allows aperture 1032 to be "locked" in place over left closing surface 1020 or right closing surface 1022 by means of left closing surface 1020 and right closing surface 1022 having a face 1020a, 1022a being a level depression whose descension 1020*b*, 1022*b* from outer annular plateau 1013 is at least equal to the length of flange 1034 and having a perimeter such that the entirety of aperture 1032 can reside within left closing surface 1020 or right closing surface 1022 and thereby creating resistance so that aperture 1032 is inhibited from moving from left closing surface 1020 or right closing surface 1022. This is to ensure that no cell 1050, 1060, 1070, 1080, 1090, 1100, 1110, 1120, 1130, 1140, 1150, 1160, 1170, 1180, 1190, 1200, 1210, 1220, 1230, 1240 is left with aperture 1032 remaining over it except by choice, to prevent aperture 1032 from sliding to a cell 1050, 1060, 1070, 1080, 1090, 1100, 1110, 1120, 1130, 1140, 1150, 1160, 1170, 1180, 1190, 1200, 1210, 1220, 1230, 1240 and enabling a tooth to escape, and to prevent dust and other particles and matter from entering the cell 1050, 1060, 1070, 1080, 1090, 1100, 1110, 1120, 1130, 1140, 1150, 1160, 1170, 1180, 1190, 1200, 1210, 1220, 1230, 1240 thereby preventing the damaging, deteriorating or dirtying of the tooth. The advantages of having two (2) closing surfaces 1020, 1022 opposite each other on the outer annular plateau 1013 are that manual manipulation of aperture 1032 to left closing surface 1020 or right closing surface 1022, requires no more than a one hundred eighty (180) degree rotation of rotatable transparent cover 1030 to place aperture 1032 over left closing surface 1020 or right closing surface 1022 and that placement of the left closing surface 1020 and right closing surface 1022 opposite each other horizontally between cell 1240 and cell 1050 and between cell 1140 and cell 1150 enhances the visual aspect of separating the teeth of the upper jaw from the teeth of the lower jaw, as well as aiding in the placement of the tooth in the appropriate cell 1050, 1060, 1070, 1080, 1090, 1100, 1110, 1120, 1130, 1140, 1150, 1160, 1170, 1180, 1190, 1200, 1210, 1220, 1230, 1240.

Adhered to and situated on the inner plateau 1015 to be seen from under the rotatable transparent cover 1030 is a customizable label and tooth indicia 1040 that displays a picture of each of the twenty (20) baby teeth in the order each tooth is located in the mouth, with the teeth of the upper jaw pictured and listed along the upper hemisphere of customizable label and tooth indicia 1040 following the curve of the upper hemisphere of customizable label and tooth indicia 1040 and the teeth of the lower jaw pictured and listed along the lower hemisphere of customizable label and tooth indicia 1040 and following along the curve of customizable label and tooth indicia 1040. The customizable label and tooth indicia 1040 is oriented on the inner plateau 1015 so that the picture of each tooth is aligned to the appropriate cell 1050, 1060, 1070, 1080, 1090, 1100, 1110, 1120, 1130, 1140, 1150, 1160, 1170, 1180, 1190, 1200, 1210, 1220, 1230, 1240.

Each cell 1050, 1060, 1070, 1080, 1090, 1100, 1110, 1120, 1130, 1140, 1150, 1160, 1170, 1180, 1190, 1200, 1210, 1220, 1230, 1240 is comprised of a base 1050*b*, 1060*b*, 1070*b*, 1080*b*, 1090*b*, 1100*b*, 1110*b*, 1120*b*, 1130*b*, 1140*b*, 1150*b*, 1160*b*, 1170*b*, 1180*b*, 1190*b*, 1200*b*, 1210*b*, 1220*b*, 1230*b*, 1240*b* opposite the cell ingress 1050*a*, 1060*a*, 1070*a*, 1080*a*, 1090*a*, 1100*a*, 1110*a*, 1120*a*, 1130*a*, 1140*a*, 1150*a*, 1160*a*, 1170*a*, 1180*a*, 1190*a*, 1200*a*, 1210*a*, 1220*a*, 1230*a*, 1240*a* and surrounding walls 1050*c*, 1060*c*, 1070*c*, 1080*c*, 1090*c*, 1100*c*, 1110*c*, 1120*c*, 1130*c*, 1140*c*, 1150*c*, 1160*c*, 1170*c*, 1180*c*, 1190*c*, 1200*c*, 1210*c*, 1220*c*, 1230*c*, 1240*c* delineating the perimeter of base 1050*b*, 1060*b*, 1070*b*, 1080*b*, 1090*b*, 1100*b*, 1110*b*, 1120*b*, 1130*b*, 1140*b*, 1150*b*, 1160*b*, 1170*b*, 1180*b*, 1190*b*, 1200*b*, 1210*b*, 1220*b*, 1230*b*, 1240*b*. Surrounding walls 1050*c*, 1060*c*, 1070*c*, 1080*c*, 1090*c*, 1100*c*, 1110*c*, 1120*c*, 1130*c*, 1140*c*, 1150*c*, 1160*c*, 1170*c*, 1180*c*, 1190*e*, 1200*c*, 1210*c*, 1220*c*, 1230*c*, 1240*c* are comprised of an outer side 1050*d*, 1060*d*, 1070*d*, 1080*d*, 1090*d*, 1100*d*, 1110*d*, 1120*d*, 1130*d*, 1140*d*, 1150*d*, 1160*d*, 1170*d*, 1180*d*, 1190*d*, 1200*d*, 1210*d*, 1220*d*, 1230*d*, 1240*d*, a right side 1050*e*, 1060*e*, 1070*e*, 1080*e*, 1090*e*, 1100*e*, 1110*e*, 1120*e*, 1130*e*, 1140*e*, 1150*e*, 1160*e*, 1170*e*, 1180*e*, 1190*e*, 1200*e*, 1210*e*, 1220*e*, 1230*e*, 1240*e*, an inner side 1050*f*, 1060*f*, 1070*f*, 1080*f*, 1090*f*, 1100*f*, 1110*f*, 1120*f*, 1130*f*, 1140*f*, 1150*f*, 1160*f*, 1170*f*, 1180*f*, 1190*f*, 1200*f*, 1210*f*, 1220*f*, 1230*f*, 1240*f* and a left side 1050*g*, 1060*g*, 1070*g*, 1080*g*, 1090*g*, 1100*g*, 1110*g*, 1120*g*, 1130*g*, 1140*g*, 1150*g*, 1160*g*, 1170*g*, 1180*g*, 1190*g*, 1200*g*, 1210*g*, 1220*g*, 1230*g*, 1240*g*.

The depth of each cell 1050, 1060, 1070, 1080, 1090, 1100, 1110, 1120, 1130, 1140, 1150, 1160, 1170, 1180, 1190, 1200, 1210, 1220, 1230, 1240 is determined by the length of each cell's 1050, 1060, 1070, 1080, 1090, 1100, 1110, 1120, 1130, 1140, 1150, 1160, 1170, 1180, 1190, 1200, 1210, 1220, 1230, 1240 surrounding walls 1050*c*, 1060*c*, 1070*c*, 1080*c*, 1090*c*, 1100*c*, 1110*c*, 1120*c*, 1130*c*, 1140*c*, 1150*c*, 1160*c*, 1170*c*, 1180*c*, 1190*c*, 1200*c*, 1210*c*, 1220*c*, 1230*c*, 1240*c* such that each tooth will lie as closely to the ingress of the cell 1050*a*, 1060*a*, 1070*a*, 1080*a*, 1090*a*, 1100*a*, 1110*a*, 1120*a*, 1130*a*, 1140*a*, 1150*a*, 1160*a*, 1170*a*, 1180*a*, 1190*a*, 1200*a*, 1210*a*, 1220*a*, 1230*a*, 1240*a* but below the level of the rotatable transparent cover 30 so that each tooth in each cell 1050, 1060, 1070, 1080, 1090, 1100, 1110, 1120, 1130, 1140, 1150, 1160, 1170, 1180, 1190, 1200, 1210, 1220, 1230, 1240 is easily visible and viewable, yet not impeding movement of rotatable transparent cover 1030.

The alternative embodiment can be easily retained by and removed from the album page by having the corners of its base inserted into the four photo retaining corners on the page.

Thus the reader will see that the present invention provides a new device which eliminates parts in prior art, combines previously uncombined features, fulfills an existing need, and satisfies a demand having a perpetual market which is not seasonal. The device is simple, convenient, durable, small, portable, marketable, novel, unique, educational, lightweight, appealing, desirable, reliable, reusable, operable, interesting, and age appropriate. It is easy to use, inexpensive to manufacture and purchase, and useful in its own right. It is a quality product with an attractive designs and shape. It provides a device necessary to display and keep baby teeth, the incomparable memento of childhood. In short, the present invention abounds with advantages and is certainly needed.

Defined in detail, the present invention is a lightweight, portable device, for retaining baby teeth, comprising: (a) a housing having a base with a bottom end, a circular plateau and a riser sidewall extending upwardly from the bottom end of the base forming into the circular plateau, then continuing to extend towards the bottom end of the base and back up to the outer plateau to form twenty (20) interior hollow chambers and two (2) shallow faces along the perimeter of circular plateau, the riser having a rib extending horizontally around the exterior of the riser sidewall, the circular plateau having a center portion lying within an area ringed by the interior hollow chambers and the shallow faces and at a height just below that of the riser sidewall, the base of the interior hollow chambers being at different depths from the top of the circular plateau in relation to the size of a baby tooth to be placed within the chamber and do not extend beyond the plane created by the bottom surface of the base, and the shallow faces located approximately 180° from each other which separate the interior hollow chambers into two groups of ten (10) interior hollow chambers; (b) an integrative surface on which the housing is incorporated, and being composed of materials to facilitate the inclusion of the integrative surface into a storage or display book; (c) a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall; (d) each interior hollow chamber sized to retain a respective one of twenty deciduous baby teeth so that each tooth can be simultaneously viewed through the transparent cover; (e) a label affixed to the upper surface of the circular plateau at least depicting each of twenty deciduous baby teeth in relation to each tooth's location in the mouth from the point of an observer and aligned in a manner that each tooth depicted correlates to a specific interior hollow chamber; and (0 a label affixed to the under-surface of the circular plateau with lines segregating the label into segments that align with and correlate to the underside bottom of each of the interior hollow chambers.

Defined broadly, the present invention is a lightweight, portable device, for retaining baby teeth, comprising: (a) a housing having a base with a bottom end, a plateau and a riser sidewall extending upwardly from the bottom end of the base forming into the circular plateau, then continuing to extend towards the bottom end of the base and back up to the plateau to form a multiplicity of interior hollow chambers and at least one shallow face along the perimeter of the plateau, the riser having a rib extending horizontally around the exterior of the riser sidewall, the plateau having a center portion lying within an area ringed by the multiplicity of interior hollow chambers and the at least one shallow face; (b) an integrative surface on which the housing is incorporated, and being composed of materials to facilitate the inclusion of the integrative surface into a storage or display book; (c) a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall; (d) each interior hollow chamber sized to retain a respective one of twenty deciduous baby teeth so that each tooth can be simultaneously viewed through the transparent cover; (e) a label affixed to the upper surface of the plateau at least depicting each of twenty deciduous baby teeth in relation to each tooth's location in the mouth from the point of an observer and aligned in a manner that each tooth depicted correlates to a specific interior hollow chamber; and (f) a label affixed to the under-surface of the plateau with lines segregating the label into segments that align with and correlate to the underside bottom of each of the interior hollow chambers.

Defined more broadly, the present invention is a lightweight, portable device, for retaining baby teeth, comprising: (a) a housing having a base with a bottom end, a plateau and a riser sidewall extending upwardly from the bottom end of the base forming into the circular plateau, then continuing to extend towards the bottom end of the base and back up to the plateau to form a multiplicity of interior hollow chambers and at least one shallow face along the perimeter of the plateau, the riser having a rib extending horizontally around the exterior of the riser sidewall, the plateau having a center portion lying within an area ringed by the multiplicity of interior hollow chambers and the shallow face; (b) an integrative surface on which the housing is incorporated, and being composed of materials to facilitate the inclusion of the integrative surface into a storage or display book; and (c) a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall.

Defined alternatively in detail, the present invention is a lightweight, portable device, for retaining baby teeth, comprising: (a) a housing having a base with a bottom end, a circular plateau and a riser sidewall extending upwardly from the bottom end of the base to forming into the circular plateau, then continuing to extend towards the bottom end of the base and back up to the circular plateau to form twenty (20) interior hollow chambers and two (2) shallow faces along the perimeter of circular plateau, the riser having a rib extending horizontally around the exterior of the riser sidewall, the circular plateau having a center portion lying within an area ringed by the interior hollow chambers and the shallow faces and at a height just below that of the riser sidewall, the base of the interior hollow chambers being at different depths from the top of the circular plateau in relation to the size of a baby tooth to be placed within the chamber and do not extend beyond the plane created by the bottom surface of the base, and the shallow faces located approximately 180° from each other which separate the interior hollow chambers into two groups of ten (10) interior hollow chambers; (b) a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall; (c) each interior hollow chamber sized to retain a respective one of twenty deciduous baby teeth so that each tooth can be simultaneously viewed through the transparent cover; (d) a label affixed to the upper surface of the circular plateau at least depicting each of twenty deciduous baby teeth in relation to each tooth's location in the mouth from the point of an observer and aligned in a manner that each tooth depicted correlates to a specific interior hollow chamber; and (e) a label affixed to the under-surface of the circular plateau with lines segregating the label into segments that align with and correlate to the underside bottom of each of the interior hollow chambers.

Defined alternatively more broadly, the present invention is a lightweight, portable device, for retaining baby teeth, comprising: (a) a housing having a base with a bottom end, a plateau and a riser sidewall extending upwardly from the bottom end of the base forming into the circular plateau, then continuing to extend towards the bottom end of the base and back up to the plateau to form a multiplicity of interior hollow chambers and at least one shallow face along the perimeter of the plateau, the riser having a rib extending horizontally around the exterior of the riser sidewall, the plateau having a center portion lying within an area ringed by the multiplicity of interior hollow chambers and the at least one shallow face; (b) a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall; (c) each interior hollow chamber sized to retain a respective one of twenty deciduous baby teeth so that each tooth can be simultaneously viewed through the transparent cover; (d) a label affixed to the upper surface of the plateau at least depicting each of twenty deciduous baby teeth in relation to each tooth's location in the mouth from the point of an observer and aligned in a manner that each tooth depicted correlates to a specific interior hollow chamber; and (e) a label affixed to the under-surface of the plateau with lines segregating the label into segments that align with and correlate to the underside bottom of each of the interior hollow chambers.

Defined alternatively even more broadly, the present invention is a lightweight, portable device, for retaining baby teeth, comprising: (a) a housing having a base with a bottom end, a plateau and a riser sidewall extending upwardly from the bottom end of the base forming into the circular plateau, then continuing to extend towards the bottom end of the base and back up to the plateau to form a multiplicity of interior hollow chambers and at least one shallow face along the perimeter of the plateau, the riser having a rib extending horizontally around the exterior of the riser sidewall, the plateau having a center portion lying within an area ringed by the multiplicity of interior hollow chambers and the shallow face; and (b) a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. A lightweight, portable device, for retaining baby teeth, comprising:
   a. a housing having a base with a bottom end, a circular plateau and a riser sidewall extending upwardly from the bottom end of the base to the circular plateau, the riser sidewall forming a part of the circular plateau, then extending downwardly towards the bottom end of the base and back up to an outer plateau to form twenty (20) interior hollow chambers and two (2) shallow faces along the perimeter of circular plateau, the riser having a rib extending horizontally around the exterior of the riser sidewall, the circular plateau having a center portion lying within an area ringed by the interior hollow chambers and the shallow faces and at a height just below that of the riser sidewall, the base of the interior hollow chambers being at different depths from the top of the circular plateau in relation to the size of a baby tooth to be placed within the chamber and do not extend beyond the plane created by the bottom surface of the base, and the shallow faces located approximately 180° from each other which separate the interior hollow chambers into two groups of ten (10) interior hollow chambers;
   b. an integrative surface on which said housing is incorporated, and being composed of materials to facilitate the inclusion of the integrative surface into a storage or display book;
   c. a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall;
   d. each interior hollow chamber sized to retain a respective one of twenty deciduous baby teeth so that each tooth can be simultaneously viewed through the transparent cover;
   e. a label affixed to the upper surface of the circular plateau at least depicting each of twenty deciduous baby teeth in relation to each tooth's location in the mouth from the point of an observer and aligned in a manner that each tooth depicted correlates to a specific interior hollow chamber; and
   f. a label affixed to the under-surface of the circular plateau with lines segregating the label into segments that align with and correlate to the underside bottom of each of the interior hollow chambers.

2. The lightweight, portable device in accordance with claim 1 wherein the center portion of the circular plateau is level with the surface of the entirety of the plateau.

3. The lightweight, portable device in accordance with claim 1 wherein the interior hollow chambers are at the same depth.

4. The lightweight, portable device in accordance with claim 1 wherein the transparent cover is situated over the upper rim of the circular plateau and affixed in a rotatable position along the upper rim of the riser sidewall and over the circular plateau.

5. The lightweight, portable device in accordance with claim 1 wherein the transparent cover having an annular shape is situated on the outer plateau and covering the openings to the interior hollow chambers.

6. A lightweight, portable device, for retaining baby teeth, comprising:
   a. a housing formed from a single piece of material having a base with a bottom end, a plateau and a riser sidewall extending upwardly from the bottom end of the base to the plateau, the riser sidewall forming a part of the plateau, then extending downwardly towards the bottom end of the base and back up to the plateau to form a multiplicity of interior hollow chambers and at least one shallow face all oriented in the same ring along the outer perimeter of the plateau, the riser having a rib extending horizontally around the exterior of the riser sidewall, the plateau having a center portion lying within an area ringed by the multiplicity of interior hollow chambers and the at least one shallow face;
   b. an integrative surface which forms into said housing and is composed of materials to facilitate the inclusion of the integrative surface into a storage or display book;
   c. a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall;
   d. each interior hollow chamber sized to retain a respective one of twenty deciduous baby teeth so that each tooth can be simultaneously viewed through the transparent cover;
   e. a label, such that it can be used in conjunction with teeth in the housing to denote the proper location for each corresponding tooth, affixed to the upper surface of the plateau at least depicting each of twenty deciduous baby teeth in relation to each tooth's location in the mouth from the point of an observer and aligned in a manner that each tooth depicted correlates to a specific interior hollow chamber;

f. a label affixed to the under-surface of the plateau with lines segregating the label into segments that align with and correlate to the underside bottom of each of the interior hollow chambers; and g. the base of the interior hollow chambers being at different depths from the top of the plateau in relation to the size of a baby tooth to be placed within the chamber.

7. The lightweight, portable device in accordance with claim 6 wherein the center portion of the plateau is level with the surface of the entirety of plateau.

8. The lightweight, portable device in accordance with claim 6 wherein the interior hollow chambers are at the same depth.

9. The lightweight, portable device in accordance with claim 6 wherein the transparent cover is situated over the upper rim of the plateau, covering the entirety of the plateau, and affixed in a rotatable position along the upper rim of the riser sidewall and over the plateau.

10. The lightweight, portable device in accordance with claim 6 wherein the transparent cover having an annular shape is situated on the plateau and over the openings to the interior hollow chambers.

11. The lightweight, portable device in accordance with claim 6 the plateau having a center portion at a height just below that of the riser sidewall.

12. A lightweight, portable device, for retaining baby teeth, comprising:
   a. a housing having a base with a bottom end, a circular plateau and a riser sidewall extending upwardly from the bottom end of the base to the circular plateau, the riser sidewall forming a part of the circular plateau, then extending downwardly towards the bottom end of the base and back up to the circular plateau to form twenty (20) interior hollow chambers and two (2) shallow faces along the perimeter of circular plateau, the riser having a rib extending horizontally around the exterior of the riser sidewall, the circular plateau having a center portion lying within an area ringed by the interior hollow chambers and the shallow faces and at a height just below that of the riser sidewall, the base of the interior hollow chambers being at different depths from the top of the circular plateau in relation to the size of a baby tooth to be placed within the chamber and do not extend beyond the plane created by the bottom surface of the base, and the shallow faces located approximately 180° from each other which separate the interior hollow chambers into two groups of ten (10) interior hollow chambers;
   b. a transparent cover having at least one aperture with a downwardly projecting flange and covering the top and sidewalls of the device and held in place by shaping itself along the sidewalls by skimming vertically down the sidewall from the top, protruding out over the rib on the sidewall and skimming down the remainder of the sidewall;
   c. each interior hollow chamber sized to retain a respective one of twenty deciduous baby teeth so that each tooth can be simultaneously viewed through the transparent cover;
   d. a label affixed to the upper surface of the circular plateau at least depicting each of twenty deciduous baby teeth in relation to each tooth's location in the mouth from the point of an observer and aligned in a manner that each tooth depicted correlates to a specific interior hollow chamber; and e. a label affixed to the under-surface of the circular plateau with lines segregating the label into segments that align with and correlate to the underside bottom of each of the interior hollow chambers.

13. The lightweight portable device in accordance with claim 12 further comprising a flat sheet having means to removably retain the lightweight portable device.

14. The lightweight, portable device in accordance with claim 12 wherein the center portion of the circular plateau is level with the surface of the entirety of circular plateau.

15. The lightweight, portable device in accordance with claim 12 wherein the interior hollow chambers are at the same depth.

16. The lightweight, portable device in accordance with claim 12 wherein the transparent cover is situated over the upper rim of the plateau and affixed in a rotatable position along the upper rim of the riser sidewall and over the circular plateau.

17. The lightweight, portable device in accordance with claim 12 wherein the transparent cover having an annular shape is situated on the circular plateau and over the openings to the interior hollow chambers.

18. A lightweight, portable device, for retaining baby teeth, comprising:
   a. a housing formed from a single piece of material having a base with a bottom end, a plateau and a riser sidewall extending upwardly from the bottom end of the base to the plateau, the riser sidewall forming a part of the plateau, then extending downwardly towards the bottom end of the base and back up to the plateau to form a multiplicity of interior hollow chambers and at least one shallow face all oriented in the same ring along the outer perimeter of the plateau, the riser having a rib extending horizontally around the exterior of the riser sidewall, the plateau having a center portion lying within an area ringed by the multiplicity of interior hollow chambers and the at least one shallow face;
   b. a transparent cover having at least one aperture with a downwardly projecting flange and covering the top and sidewalls of the device and held in-place by shaping itself along the sidewalls by skimming vertically down the sidewall from the top, protruding out over the rib on the sidewall and skimming down the remainder of the sidewall;
   c. each interior hollow chamber sized to retain a respective one of twenty deciduous baby teeth so that each tooth can be simultaneously viewed through the transparent cover;
   d. a first label, such that it can be used in conjunction with teeth in the housing to denote the proper location for each corresponding tooth, affixed to the upper surface of the plateau at least depicting each of twenty deciduous baby teeth in relation to each tooth's location in the mouth from the point of an observer and aligned in a manner that each tooth depicted correlates to a specific interior hollow chamber;
   e. a second label, such that it can be used in conjunction with teeth in the housing, affixed to the under-surface of the plateau with lines segregating the label into segments that align with and correlate to the underside bottom of each of the interior hollow chambers; and
   f. the base of the interior hollow chambers being at different depths from the top of the plateau in relation to the size of a baby tooth to be placed within the chamber.

19. The lightweight portable device in accordance with claim 18 further comprising a flat sheet having means to removably retain the lightweight portable device.

20. The lightweight, portable device in accordance with claim 18 wherein the center portion of the plateau is level with the surface of the entirety of plateau.

21. The lightweight, portable device in accordance with claim 18 wherein the interior hollow chambers are at the same depth.

22. The lightweight, portable device in accordance with claim 18 wherein the transparent cover is situated over the upper rim of the plateau, covering the entirety of the plateau, and affixed in a rotatable position along the upper rim of the riser sidewall and over the plateau.

23. The lightweight, portable device in accordance with claim 18 wherein the transparent cover having an annular shape is situated on the plateau and over the openings to the interior hollow chambers.

24. The lightweight, portable device in accordance with claim 18 the plateau having a center portion at a height just below that of the riser sidewall.

* * * * *